United States Patent
Eloit et al.

(10) Patent No.: US 7,109,025 B1
(45) Date of Patent: Sep. 19, 2006

(54) VIRAL VECTORS AND VIRAL VACCINES BASED ON RECOMBINANT PORCINE ADENOVIRUSES

(75) Inventors: Marc Eloit, St Maur (FR); Bernard Georges Klonjkowski, Paris (FR)

(73) Assignees: Merial, Lyons (FR); Ecole Nationale Veterinaire de Maison Alfort, Maisons (FR)

( * ) Notice: Subject to any disclaimer, the term of this patent is extended or adjusted under 35 U.S.C. 154(b) by 0 days.

(21) Appl. No.: 09/913,249

(22) PCT Filed: Feb. 8, 2000

(86) PCT No.: PCT/FR00/00294

§ 371 (c)(1),
(2), (4) Date: Aug. 10, 2001

(87) PCT Pub. No.: WO00/47756

PCT Pub. Date: Aug. 17, 2000

(30) Foreign Application Priority Data

Feb. 11, 1999 (FR) ................................... 99 01813

(51) Int. Cl.
*C12N 15/00* (2006.01)

(52) U.S. Cl. ............................. 435/320.1; 435/235.1; 424/184.1; 424/202.1; 424/204.1; 424/233.1

(58) Field of Classification Search .............. 435/235.1, 435/320.1; 424/184.1, 202.1, 204.1, 233.1
See application file for complete search history.

(56) References Cited

U.S. PATENT DOCUMENTS 6,492,343 B1 * 12/2002 Reddy et al. .................. 514/44

FOREIGN PATENT DOCUMENTS

| WO | WO 97/20036 | 6/1997 |
| WO | WO 99/08706 | 2/1999 |
| WO | WO 99/53047 | 10/1999 |

OTHER PUBLICATIONS

Reddy Virus Research 1995, vol. 37, pp. 97-106.*
Zakhartchouk 1998 Virology 250: 220-229.*
Tuboly 1995 Virus Research 37: 49-54.*
Tuboly Virus Research 1995, vol. 367, pp. 49-54.*
Reddy, et al., "Development of porcine adenovirus-3 as an expression vector," Journal of General Virology, (1990), 80, pp. 563-570.
Torres, et al., "Tropism of Human Adenovirus Type 5-Baed Vectors in Swine and Their Ability to Protect Against Transmissible Gastroenteritis Coranavirus," Journal of Virology, Jun. 1996, pp. 3370-3780.
Reddy, et al., "Porcine adenoviruses types 1, 2 and 3 have short and simple early E-3 regions," Virus Research 43 (1996), pp. 99-109.
Reddy, et al., "Sequence analysis of putative pVIII, E3 and fibre regions of porcine adenovirus type 3," Virus Research 36 (1995), pp. 97-106.
Kleiboeker, Steven B., "Sequence analysis of putative E3, pVIII, and fiber genomic regions of a porcine adenovirus," Virus Research 31 (1994), pp. 17-25.
Tuboly, et al., "Restriction endonuclease analysis and physical mapping of the genome of porcine adenovirus type 5," Virus Research 37 (1995), pp. 49-54.
Mittal, et al., "Development of a bovine adenovirus type 3-based expression vector," Journal of General Virology 76 (1995), pp. 93-102.
Reddy, et al., "Restriction Endonuclease Analysis and Molecular Cloning of Porcine Adenovirus Type 3," Intervirology 36 (1993), pp. 161-168.

* cited by examiner

*Primary Examiner*—James Housel
*Assistant Examiner*—Myron G. Hill
(74) *Attorney, Agent, or Firm*—Frommer Lawrence & Haug LLP; Thomas J. Kowalski; Judy Jarecki-Black

(57) ABSTRACT

An in vivo replicative and recombined porcine adenovirus characterized in that it comprises a heterologous nucleotide sequence inserted into the porcine adenovirus in conditions enabling the latter to be replicated in vivo and to express the inserted heterologous nucleotide sequence, and in that the adenovirus genome comes from a 3 or 5 serotype (PAV-3 or PAV-5) adenovirus. Insertion occurs in a non-essential zone of the E3 region, preferably with deletion of said zone. The invention also relates to a recombined porcine vaccine comprising one such porcine adenovirus. The invention further relates to a serotype 3 or 5 porcine adenovirus vector that is replicative in vivo and is deleted in a non-essential region of the genome thereof. The invention also relates to a DNA fragment comprising all or part of the referenced SEQ ID NO.5 nucleotide sequence.

Figure 1:
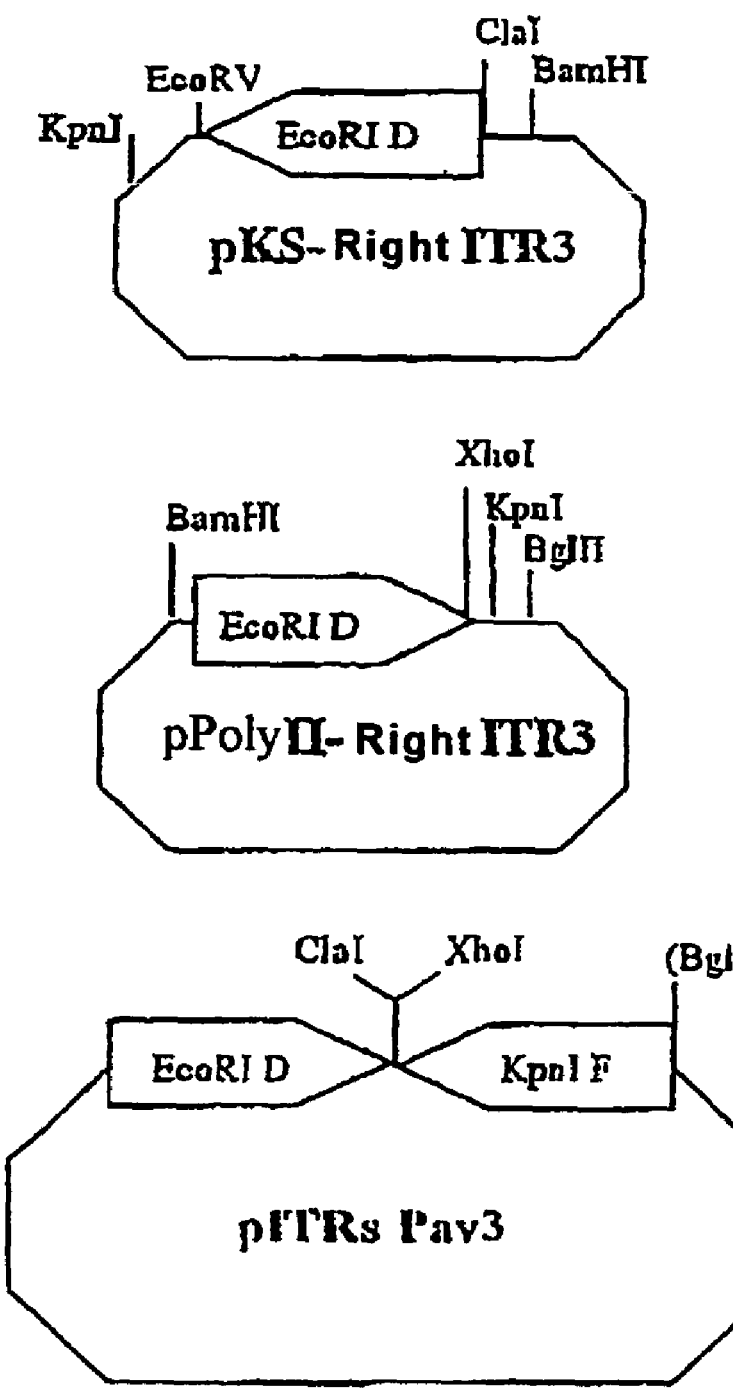

45 Claims, 14 Drawing Sheets pE3 dl 622 gD pE3 dl 919 CMV-gD

Physical Map of PAV-5, BamHI digestion
(from Tubolt et al. Virus Research 37 (1995) 49-54)

AAGCTTCTCTGCCAGATTTAACGAGCCAAAGCATGATGCAGCAATTTAGAAACTTTACCCTCGAAAGGTCTGGCA
TTCTTCCGGCCTGCTGCAACGCCTTTCCCACGGACTTTGTACCCATCACCTATAAAGAATGCCCACCCCTCTCT
GGGGATACTGCTACCTCATGAGGCTGGCCAACTTTATCATGTTCCACACCGATGTGGCTTACAACATGGAAGGGG
AGGGCTTGTTCGAATGCTATTCCCGGTGCAACCTTTGCACCCCTCACCGATGCTTGGCCACCAACACCGCCCTGT
TAAACGAGGTTCAGGCCATCGGCACTTTCGAACTTCAAGGTCCACCAAACGAGGATGGGTCCATGCCACACCCAC
TCAAACTCACGGCCGGCGCCTGGACGAGCGCCTACCTTAAAAAGTTTGAGGAAAAAGACTACTGTCACCACACCA
TCCAATTTTACGAAGACCAATCAAAAGCACCCAAAGCAGAGTTGACCGCCTGTGTCATCACTCAAGCCGCCATCC
TCGCCCAATTACATGACATTAAAAAAGCGCGGGAAAACTTCCTCCTTAAAAAGGGGCACGGGGTATACCTCGACC
CACAGACCGGAGAGGAACTCAACACGTCCACCCCCTCCGCCGCCAACAATGCCGAAGCTAAAAACTCCTCGACCG
GGTTCCCTAAATCTGACAAACCCCATCATGAAGAAGAGCAGAAAAACCAAACAGATTCTGCCGCCGCCTCCTCCA
ACTCCAGAAGAAGAGGAGATTATAGACGAGGAGGCCGAGGAATGGGACGAAGAGAGCATGGATTCTCAGGAAGGA
TTGGAAACCATCGAAGAGCTGGAGGAAGGGGAAATCCCTCCTACCCCTCCAACCATTCCCAAAAAGCAGCGTAGA
TGGGATCAGAAACCCGAATTGATCAACGCGCAGACCGGAGGTAAGGCCGAGTCAAGATATAAGTCCTGGCGCAGA
TACAAAAATATTATTTATAAAACCCTGATGGCCAGCGGCTACGACGTCTCTTTCGCGCGCCGCTATCTTCTGTTC
AGACACGGGGTCAATATTCCGAAAAATGTAATCCATTACTACAATTCCCACTGCAGAAACCAAGACCCCGAAGAA
GTCTGGAAGGAAATCCATCCAGTCTGCCAATATATCCAAAGAACCAGCGACGACCAGAGCGCTAAGAGCTAGGAT
CTTTCCCACGTTGTATGCCATCTTCCAGCAGAGCCGCGGAGTAGACAGCAACCTCAAGGTTAAAAACAGATCACT
TCGCTCTCTCACCAAAAGCTGCTTGTATCACAACCAGGAATCTCAGCTTCAAAGAACCTTAGAGGACGCTGAAGC
TCTCCTTCACAAGTACTGCTCCGGTCTGACTGCCTCCTCTTATAATGAGTAAAGACATCCCCACCCCTTACGTGT
GGACCTATCAGCCTCAGCTACGTCAGGCGGCTGGCGCGTCACAAGACTACTCCACCCGCATGAATTGGCTAAGTG
CCGGACCGTCAATGATTGACCAGGTGAATCAGATAAGGGTGGAACGCAATAATATTTTATTGCGGCAGGCGGCGG
CCACGGAGACGCCCAGGTTAGTGCGGAATCCACCCAACTGGCCCGCACGCTACCTGTACCAGCCCATGGGTGCGC
CGCAAACAGTGGAACTTCCGCGTAATGAGTTACTCGAAACCGTCATGACTAACTCTGGAATGCAGTTGGCGGGCG
GAGGTCGCACTACCTGCGGTATAAAAGGAGCACACCTGAGCGGCTCAGGTATTCAGCTCAACGGAGAGCTACCGA
GCGCCTCTTGGCTGAGACCTGACGGAGTCTTCCAGCTAGCTGGTGGCAGCCGTTCTTCTTTCAGCCCAGGCGTCA
GCACTCTGCTGAGACTAGAACCATCTTCCTCCCTACCGAGATCCGGTGGGATTGGAAGCACCCAATTCGTTCAAG
AGTTTGTTCCAGCCGTCTACTTTCAGCCTTTCTCCGGACCACCTGGAACATATCCTGACGAATTCATCTACAACT
ACGACATAGTCTCTGACTCTGTCGACGGTTATGACTGATAGAGACGCCAGACTTGCTGTCACCGCTCTCTCATCC
CTGCATCAAGAGACCTGCAAGAGAAGCCACTGCTTCACCAAGGCCGACCTCAACCTAGCCTACTTCTGTGTGCTG
CCCAGCGACCTTGAAGATGATTGTGTGCCTGACTCCCTCCAAGTCGGACACGGGCTTCGGCTTGAGCTTCCGTAC
TGCTTCAAAAGCTTTTTCATCTTTAAGGGAGGAAAAAAATACCTCTGCAGCGAACACCTCCAAAATGGCCACCTC
AAAGTCTCGTGCGACTGCGCCTCCCCTGGCGCCCATCTCGACATGTTTGACACACTTTGCCAGCTGTATAACAAC
ACTGCTCCTCGTCCTGATTCTGTCTCATCTGACTCCGACGACTGAAGCCGCCCAGCCAGAAGTGCGCATCAAGGC
GGTCACTTACGACTGGCTGTGTGTGCTTGACATCAACTGCACTCACCAGCAGCCTGTACACTTAAAATGGAAGGG
GTATGATTACAAGACAAGCCATCTCACCATCAAAGCAAACTCAGACATCTCAGACGAGCCCGTCATGTGTACCAC
AGACAACCATCCCAGAGAAACGGCCACTGTTGACATTCGAGACCACTGCAAATTTCCACCGACCGTTAGATACAT
GCTGAAGAAAGTCCTACCCATCTACTTCACCTTTCTGTCAGGTGTGATGCTATGTCTCGTGTTTCCTGCAGCTAG
ATACCCATCACTTCTGTCGGCTCTTCCAGTTGCCATGGCTAGCACCACATCTAGCATCACTACTGATGTGAGTAC
TCTGTCAAACTACTCCAGCGAACAATCTACAACCGAACATCCAACCACAGCAAATTCACAGCCTTACACGGCCGT

FIG. 13A

FIG. 13 | FIG. 13A / FIG. 13B

```
GGAGAAGACACTGCTTGCTTTGATTCCGATCCTCATTGCCTGCATTGTAATGGTGCTTGTTTTCACATTTCTGCT
AAAGAAGAAACAGAAGGAAGTAAATGACGCTGGAGTCTACCCCATATACAGACCAAGAAGGTCGTCATCCATGTC
AAAGCTAACACTTATTACTACACTGTGTTTACTGGCAACCGCAAACTGCGAAAAACACTACAAATCTTATGTTGA
AGGAGAAAACGCCTATCTTGAAAATCTATTTAACAACTACTGTGAGCTAAAGTGGTATTGGTTTTATACGAGACA
TGAGGGATATGTTTTGGCAAAACGCGATGGCGACCACACTCGTACATTTGATTTAAAACCAAAAAACATGTATGT
AGATGAAGATACTTTTGACCTGATTATAAGAAACATTGAAGTAAAAAACACTGGAATGTATGAAGTAGAATATCA
CTGTGGCACATATACAAGGTCTGAGTACTATGTAGTCACAGTTCTTCCAAACATCGCAGAATCATCTCTAAACGT
TGAATCTGTGTCTATCAACGGCAGCATTTGTCAAATCTCTTTACATTGTGGCATCGAGAACAACTTAGTGGAAAC
AAGAATTATATATGAGGACAATGTCATTAGTGACAACAATCTTATGCTCAGCTTGAACATCTCTAAAGAACCCAG
CACACTCACTTGCTTTACTAACACTTCTAAACAATCTGTAAAACTAAGTTTGAATATATCTGATTATTGCAAACA
ACCTAATTCAAAACATGAAAAAATCATCCTAAGTGAAGATTCTTCAGAAAATGAAAAGAAGCAAATAATCGTTTT
TTCGGTCACAGCGGCAGTTGCATTCCTAATGATTATTCTACTGATAATATCTTTCAAACCAAGACTTTGCTTCGG
AACTCCAGTATATGCAGTCGTATTGGCTGCCACAGGGGCAGAAGCCTCAAATTGTACTTGTGCTGATGTTAACAA
CGATTGGTCATATGTCCTAGTTATCATTCTTTCAACTCTAACTTGTATCAGTCTAATTGTTGGAATTCTAAAGAT
TATTTTTCTTTGCCTCTTCCGCTGCCCAGGCAATCATGATGATGATGATGTCTAATTGAAATCACTAATAAAGAT
TTCTAAACTAAAATTGGCTTTTTCGTTTTTAGCATGAAACGCGCAAAGAGATCAATACCTACAGACTTTGATCCG
GTTTATCCATACGGGAACCCACCACTTAACATAATTCCTCCATTTTACAGTACAGATGGTTTTCAAGAGTTCCCA
GTTACAACACTATCTCTTAAAGTAGACGACCCTGTTACCTTTTCCAACACTGGGGGCATCACACTGAAATTGGGT
GGTGGTGTTAGCATCAACCAAAACGGAGAACTAGAATCATCGTCCGTACCAACTATACTAAATCCACCACTTGAC
AATTCCAACGGATCCCTTAGCTTAAATATAGGAGAGGGTTTACAGGAAAGCAATGGAGCACTTGTACTCTACAAA
GAACCACCATTCATTTTCTCAAGCAACGCGCTAGGTATAGATTTGGGTAATGGCATGCAGCTATCGGCAGATAAA
CTGTCACTAAAATTGGGAAACGGCTTATCCTTTTCATCAGATGGCTCCTTACAAGTTCAAACTTCACCGCCTCTG
ATAAATGGGTCAAGTATTGGTCTAAACATCGCAAACCCTTTTTCAATAGACTCAAATCAGGCATTGTCTTTGCAA
ACGGAATCATATTTTTCTACAAACAACTCACTTTCTTTAAATGTTGGAGATGGATTGCAAACCACAAACAACCAG
CTATCGCTTCAGGTGTCACCTTACTTTGGGTTTTCATCTGGGTCCCTGTCCTTATCCATTGCTAACATGATGAAC
CTCAGGAACAACACTCTAGGAGTAAATGTTGGCAACGGCCTGTTTGTTAATCCTTCGAACGCAATAGCTGTCAAT
GTTAGAGCGCCTTTAAACTATAGCGGTACTACAAAATCCGTAACCGTTGTAGCCGGACCAGGCCTCACCATCAGC
GGGGAAACACTTGGCTCTGATATAAGAGTGAATGCTGGCAATGGGTTGTTTGCTGATACACAAAATGTAAGGGTA
AAACTAGGTGCCGGGCTTATTTTTGACTCAAATGGAAATATTCAAGTAAATGTGGGTTCTGGATTGCAAATACAG
AACAATGCTGTGGTGGTGGCCTCATCTACCAACACCTCCTCATCCATTGCAAGTTACTCAGCAAGTTCAGCATCT
ACTCCCACATCGACATCGCCCACTAGCGGGACATATCTCTACAACTATCAAATAGCCTTTAGTTGGGACATTGTA
GAAACCGATCAAAACTATTTCATCTACACGCTCAGATGCACCGAGATTACGCCTCAAAATAATCAGGTCGAACTC
AGCTTCACACCGACAGACCCAAACTTTATAAGTTTCTTTGACTACATAAACACGATGCACACCGTTGCGCATCAA
ATTTCTGGTTCTACTGTAACCAATATACCCATCACCGTGACGTACAGTAATTCTAGCAACCAACTGAGGATTATC
TTCTCCTCCACGGTGGTTAAAAACCTAACAATGACACCTTGGGTGGCGAGCGTTGTCAGGCATAAAGCAACCATT
ACTAGTGGAAGTGCGTGGATGGGCACGGCTTGGTAGCCGGCTTACCTGTAAAGTTTAAACGCGT
```

FIG. 13B

| FIG. 13 | FIG. 13A |
|---------|----------|
|         | FIG. 13B |

SEQUENCE LISTING

<160> NUMBER OF SEQ ID NOS: 6

<210> SEQ ID NO 1
<211> LENGTH: 50
<212> TYPE: DNA
<213> ORGANISM: Artificial Sequence
<220> FEATURE:
<223> OTHER INFORMATION: Oligonucleotide ITRPAV3

<400> SEQUENCE: 1
ccttaattaa ggtagggata acagggtaat catcatcaat aatataccgc          50

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide T3
<220> FEATURE:
<221> NAME/KEY: misc_feature
<222> LOCATION: (1)..(20)
<223> OTHER INFORMATION: T3 universal primer

<400> SEQUENCE: 2
attaaccctc actaaaggga          20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide T7
<220> FEATURE:
<221> NAME/KEY: misc_feature
<222> LOCATION: (1)..(20)
<223> OTHER INFORMATION: T7 universal primer

<400> SEQUENCE: 3
taatacgact cactataggg          20

<210> SEQ ID NO 4
<211> LENGTH: 50
<212> TYPE: DNA
<213> ORGANISM: Artificial Sequence
<220> FEATURE:
<223> OTHER INFORMATION: Oligonucleotide ITRPAV5

<400> SEQUENCE: 4
ccttaattaa ggtagggata acagggtaat catcatcaat aatatacgga          50

-continued

```
<210> SEQ ID NO 5
<211> LENGTH: 5614
<212> TYPE: DNA
<213> ORGANISM: Porcine adenovirus 5

<400> SEQUENCE: 5
aagcttctct gccagattta acgagccaaa gcatgatgca gcaatttaga aactttaccc      60
tcgaaaggtc tggcattctt ccggcctgct gcaacgcctt tcccacggac tttgtaccca     120
tcacctataa agaatgccca cccctctct ggggatactg ctacctcatg aggctggcca      180
actttatcat gttccacacc gatgtggctt acaacatgga aggggagggc ttgttcgaat     240
gctattgccg gtgcaacctt tgcaccctc accgatgctt ggccaccaac accgccctgt      300
taaacgaggt tcaggccatc ggcactttcg aacttcaagg tccaccaaac gaggatgggt     360
ccatgccaca cccactcaaa ctcacggccg gcgcctggac gagcgcctac cttaaaaagt     420
ttgaggaaaa agactactgt caccacacca tccaattta cgaagaccaa tcaaaagcac      480
ccaaagcaga gttgaccgcc tgtgtcatca ctcaagccgc catcctcgcc caattacatg     540
acattaaaaa agcgcgggaa aacttcctcc ttaaaaaggg gcacggggta tacctcgacc     600
cacagaccgg agaggaactc aacacgtcca cccctccgc cgccaacaat gccgaagcta      660
aaaactcctc gaccgggttc cctaaatctg acaaacccca tcatgaagaa gagcagaaaa     720
accaaacaga ttctgccgcc gcctcctcca actccagaag aagaggagat tatagacgag     780
gaggccgagg aatgggacga agagagcatg gattctcagg aaggattgga aaccatcgaa     840
gagctggagg aaggggaaat ccctcctacc cctccaacca ttcccaaaaa gcagcgtaga     900
tgggatcaga aacccgaatt gatcaacgcg cagaccggag gtaaggccga gtcaagatat     960
aagtcctggc gcagatacaa aaatattatt tataaaaccc tgatggccag cggctacgac    1020
gtctctttcg cgcgccgcta tcttctgttc agacacgggg tcaatattcc gaaaaatgta    1080
atccattact acaattccca ctgcagaaac caagaccccg aagaagtctg gaaggaaatc    1140
catccagtct gccaatatat ccaaagaacc agcgacgacc agagcgctaa gagctaggat    1200
ctttcccacg ttgtatgcca tcttccagca gagccgcgga gtagacagca acctcaaggt    1260
taaaaacaga tcacttcgct ctctccaccaa agctgcttg tatcacaacc aggaatctca     1320
gcttcaaaga accttagagg acgctgaagc tctccttcac aagtactgct ccggtctgac    1380
tgcctcctct tataatgagt aaagacatcc caccccctta cgtgtggacc tatcagcctc    1440
agctaggtca ggcggctggc gcgtcacaag actactccac ccgcatgaat tggctaagtg    1500
ccggaccgtc aatgattgac caggtgaatc agataagggt ggaacgcaat aatattttat    1560
tgcggcaggc ggcggccacg gagacgccca ggttagtgcg gaatccaccc aactggcccg    1620
cacgctacct gtaccagccc atgggtgcgc cgcaaacagt ggaacttccg cgtaatgagt    1680
tactcgaaac cgtcatgact aactctggaa tgcagttggc gggcggaggt cgcactacct    1740
gcggtataaa aggagcacac ctgagcggct caggtattca gctcaacgga gagctaccga    1800
gcgcctcttg gctgagacct gacggagtct tccagctagc tggtggcagc cgttcttctt    1860
tcagcccagg cgtcagcact ctgctgagac tagaaccatc ttcctcccta ccgagatccg    1920
gtgggattgg aagcacccaa ttcgttcaag agtttgttcc agccgtctac tttcagcctt    1980
tctccggacc acctggaaca tatcctgacg aattcatcta caactacgac atagtctctg    2040
actctgtcga cggttatgac tgatagagac gccagacttg ctgtcaccgc tctctcatcc    2100
ctgcatcaag agacctgcaa gagaagccac tgcttcacca aggccgacct caacctagcc    2160
```

-continued

```
tacttctgtg tgctgcccag cgaccttgaa gatgattgtg tgcctgactc cctccaagtc    2220
ggacacgggc ttcggcttga gcttccgtac tgcttcaaaa gcttttttcat ctttaaggga   2280
```

```
tacttctgtg tgctgcccag cgaccttgaa gatgattgtg tgcctgactc cctccaagtc    2220
ggacacgggc ttcggcttga gcttccgtac tgcttcaaaa gctttttcat ctttaaggga    2280
ggaaaaaaat acctctgcag cgaacacctc caaaatggcc acctcaaagt ctcgtgcgac    2340
tgcgcctccc ctggcgccca tctcgacatg tttgacacac tttgccagct gtataacaac    2400
actgctcctc gtcctgattc tgtctcatct gactccgacg actgaagccg cccagccaga    2460
agtgcgcatc aaggcggtca cttacgactg gctgtgtgtg cttgacatca actgcactca    2520
ccagcagcct gtacacttaa aatggaaggg gtatgattac aagacaagcc atctcaccat    2580
caaagcaaac tcagacatct cagacgagcc cgtcatgtgt accacagaca accatcccag    2640
agaaacggcc actgttgaca ttcgagacca ctgcaaattt ccaccgaccg ttagatacat    2700
gctgaagaaa gtcctaccca tctacttcac ctttctgtca ggtgtgatgc tatgtctcgt    2760
gtttcctgca gctagatacc catcacttct gtcggctctt ccagttgcca tggctagcac    2820
cacatctagc atcactactg atgtgagtac tctgtcaaac tactccagcg aacaatctac    2880
aaccgaacat ccaaccacag caaattcaca gccttacacg gccgtggaga agacactgct    2940
tgctttgatt ccgatcctca ttgcctgcat tgtaatggtg cttgttttca catttctgct    3000
aaagaagaaa cagaaggaag taaatgacgc tggagtctac cccatataca gaccaagaag    3060
gtcgtcatcc atgtcaaagc taacacttat tactacactg tgtttactgg caaccgcaaa    3120
ctgcgaaaaa cactacaaat cttatgttga aggagaaaac gcctatcttg aaaatctatt    3180
taacaactac tgtgagctaa agtggtattg gttttatacg agacatgagg gatatgtttt    3240
ggcaaaacgc gatggcgacc acactcgtac atttgattta aaaccaaaaa acatgtatgt    3300
agatgaagat acttttgacc tgattataag aaacattgaa gtaaaaaaca ctggaatgta    3360
tgaagtagaa tatcactgtg gcacatatac aaggtctgag tactatgtag tcacagttct    3420
tccaaacatc gcagaatcat ctctaaacgt tgaatctgtg tctatcaacg gcagcatttg    3480
tcaaatctct ttacattgtg gcatcgagaa caacttagtg gaaacaagaa ttatatatga    3540
ggacaatgtc attagtgaca acaatcttat gctcagcttg aacatctcta agaacccag    3600
cacactcact tgctttacta acacttctaa acaatctgta aaactaagtt tgaatatatc    3660
tgattattgc aaacaaccta attcaaaaca tgaaaaaatc atcctaagtg aagattcttc    3720
agaaaatgaa aagaagcaaa taatcgtttt ttcggtcaca gcggcagttg cattcctaat    3780
gattattcta ctgataatat cttctcaaacc aagactttgc ttcggaactc cagtatatgc    3840
agtcgtattg gctgccacag gggcagaagc ctcaaattgt acttgtgctg atgttaacaa    3900
cgattggtca tatgtcctag ttatcattct ttcaactcta acttgtatca gtctaattgt    3960
tggaattcta aagattattt ttcttttgcct cttccgctgc ccaggcaatc atgatgatga    4020
tgatgtctaa ttgaaatcac taataaagat ttctaaacta aaattggctt tttcgtttt    4080
agcatgaaac gcgcaaagag atcaatacct acagactttg atccggttta ccatacgggg   4140
aacccaccac ttaacataat tcctccattt tacagtacag atggttttca agagttccca    4200
gttacaacac tatctcttaa agtagacgac cctgttacct tttccaacac tgggggcatc    4260
acactgaaat tgggtggtgg tgttagcatc aaccaaaacg agaactaga atcatcgtcc    4320
gtaccaacta tactaaatcc accacttgac aattccaacg gatcccttag cttaaatata    4380
ggagagggtt tacaggaaag caatggagca cttgtactct acaaagaacc accattcatt    4440
ttctcaagca acgcgctagg tatagatttg ggtaatggca tgcagctatc ggcagataaa    4500
ctgtcactaa aattgggaaa cggcttatcc ttttcatcag atggctcctt acaagttcaa    4560
```

-continued

| | |
|---|---|
| acttcaccgc ctctgataaa tgggtcaagt attggtctaa acatcgcaaa cccttttca | 4620 |
| atagactcaa atcaggcatt gtctttgcaa acggaatcat attttctac aaacaactca | 4680 |
| ctttctttaa atgttggaga tggattgcaa accacaaaca accagctatc gcttcaggtg | 4740 |
| tcaccttact ttgggttttc atctgggtcc ctgtccttat ccattgctaa catgatgaac | 4800 |
| ctcaggaaca acactctagg agtaaatgtt ggcaacggcc tgtttgttaa tccttcgaac | 4860 |
| gcaatagctg tcaatgttag agcgccttta aactatagcg gtactacaaa atccgtaacc | 4920 |
| gttgtagccg gaccaggcct caccatcagc ggggaaacac ttggctctga tataagagtg | 4980 |
| aatgctggca atgggttgtt tgctgataca caaaatgtaa gggtaaaact aggtgccggg | 5040 |
| cttattttg actcaaatgg aaatattcaa gtaaatgtgg gttctggatt gcaaatacag | 5100 |
| aacaatgctg tggtggtggc ctcatctacc aacacctcct catccattgc aagttactca | 5160 |
| gcaagttcag catctactcc cacatcgaca tcgcccacta gcgggacata tctctacaac | 5220 |
| tatcaaatag cctttagttg ggacattgta gaaaccgatc aaaactattt catctacacg | 5280 |
| ctcagatgca ccgagattac gcctcaaaat aatcaggtcg aactcagctt cacaccgaca | 5340 |
| gacccaaact ttataagttt ctttgactac ataaacacga tgcacaccgt tgcgcatcaa | 5400 |
| atttctggtt ctactgtaac caatataccc atcaccgtga cgtacagtaa ttctagcaac | 5460 |
| caactgagga ttatcttctc ctccacggtg gttaaaaacc taacaatgac ccttgggtg | 5520 |
| gcgagcgttg tcaggcataa agcaaccatt actagtggaa gtgcgtggat gggcacggct | 5580 |
| tggtagccgg cttacctgta aagtttaaac gcgt | 5614 |

<210> SEQ ID NO 6
<211> LENGTH: 34094
<212> TYPE: DNA
<213> ORGANISM: Porcine adenovirus 3

<400> SEQUENCE: 6

| | |
|---|---|
| catcatcaat aatataccgc acactttat tgccccttt gtggcgtggt gattggcgga | 60 |
| gagggttggg ggcggcgggc ggtgattggt ggagagggt gtgacgtagc gtgggaacgt | 120 |
| gacgtcgcgt gggaaaatga cgtgtgatga cgtcccgtgg aacgggtca agtccaagg | 180 |
| ggaaggggtg gagccctggg gcggtcctcc gcggggcggg gccgagcggc ggaaattccc | 240 |
| gcacaggtgg agagtaccgc gggattttgt gccctctgga ccggaccttc gccctccggt | 300 |
| gtggcacttc cgcaccacac gtccgcggcc cggtattccc cacctgacga cggtgacacc | 360 |
| actcacctga gcgggtgtc cttcgcgctg agaggtccgc ggcggccgcc cgagatgacg | 420 |
| tgtgtgggtg tattttttcc cctcagtgta tatagtccgc gcagcgcccg agagtcacta | 480 |
| ctcttgagtc cgaagggagt agagttttct ctcagcggaa cagaccctcg acatggcgaa | 540 |
| cagacttcac ctggactggg acggaaaccc cgaggtggtg ccggtgctgg aatgggaccc | 600 |
| ggtggatctg cgcgacccct ctccggggga tgagggcttc tgtgagccgt gctgggagag | 660 |
| tctggtcgat ggactgccgg acgagtggct ggacagtgtg gacgaggtgg aggtgattgt | 720 |
| gactgagggg ggtgagtcag aggacagtgg tgggagtgcc gctggtgact caggtggctc | 780 |
| tcagggggtc tttgagatgg acccccccaga agaggggac agtaatgagg aggatatcag | 840 |
| cgcggtggct gcgaggtgc tgtctgaact ggctgatgtg gtgtttgagg cccacttgc | 900 |
| gccaccctct ccgtttgtgt tggactgccc cgaggtacct ggtgtgaact gccgctcttg | 960 |
| tgattaccat cgctttcact ccaaggaccc caatctgaag tgcagtctgt gctacatgag | 1020 |
| gatgcatgcc tttgctgtct atggtgagtg ttttttggaca tttgtgggat tatgtggaaa | 1080 |

```
aaaaggaaaa agtgcttgta agaaatctca tgtgctatttt cccattttttt gtctttttag   1140 aagctgtttc tccagcacct cacaggtcgg gttccccggg acttggagac ctgccaggac   1200
gcaagaggaa gtactgctat gactcatgca gcgaacaacc tttggacctg tctatgaagc   1260
gcccccgcga ttaatcatta acctcaataa acagcatgtg atgatgactg attgtctgtg   1320
tctctgccta tatacccct tgtggtttgc agggaaggga tgtggtgact gagctattcc   1380
tcagcatcat catcgctctg cttttttcta ctgcaggcta tttcttgcta gctcgctgtc   1440 cctttttcttt ttctgtgggc atggactatc aacttctggc caagcttact aacgtgaact   1500
accttaggaa ggtgatagta cagggtctc agaactgccc ttggtggaaa agatttttt   1560 cggacaggtt tatcaaggta gtagcagagg ccaggaggca gtacgggcaa gagttgattg   1620 agattttttgt ggagggtgag agggctttg gtcctgagtt cctgcgggaa ggggactgt   1680 acgaagaggc cgttctgaaa gagttggatt tcagcacctt gggacgcacc gtagctagtg   1740
tggctctggt ctgcttcatt tttgagaagc ttcagaagca cagcgggtgg actgacgagg   1800
gtattttaag tcttctggtg ccgccactat gttccctgct ggaggcgcga atgatggcgg   1860
agcaggtgcg gcaggggctg tgcatcatca ggatgccgag cgcggagcgg gagatgctgt   1920
tgcccagtgg gtcatccggc agtggcagcg gggccgggat gcgggaccag gtggtgccca   1980
agcgcccgcg ggagcaggaa gaggaggagg aggacgagga tgggatggaa gcgagcgggc   2040
gcaggctcga agggccggat ctggtttaga tcgccgccgg cccgggggag cgggtggaga   2100
ggggagcggg gaggaggcgg gggggtcttc catggttagc tatcagcagg tgctttctga   2160
gtatctggag agtcctctgg agatgcatga gcgctacagc tttgagcaga ttaggcccta   2220
tatgcttcag ccggggggatg atctggggga gatgatagcc cagcacgcca aggtggagtt   2280
gcagccgggc acggtgtacg agctgaggcg cccgatcacc atccgcagca tgtgttacat   2340
catcgggaac ggggccaaga tcaagattcg ggggaattac acggagtaca tcaacataga   2400
gccgcgtaac cacatgtgtt ccattgcggg catgtggtcg gtgactatca cggatgtggt   2460
ttttgatcgg gagctaccgg cccggggtgg tctgattttta gccaacacgc acttcatcct   2520
gcacggctgc aacttcctgg gctttctggg ctcggtaata acggcgaacg ccgggggggt   2580
ggtgcgggga tgctactttt tcgcctgcta caaggcgctg gaccaccggg ggcggctgtg   2640
gctgacggtg aacgagaaca cgtttgaaaa gtgtgtgtac gcggtggtct ctgcggggcg   2700
ttgcaggatc aagtacaact cctccctgtc caccttctgc ttcttgcaca tgagctatac   2760
gggcaagata gtggggaaca gcatcatgag cccttacacg ttcagcgacg accccctacgt   2820 ggacctggtg tgctgccaga gcgggatggt gatgccccctg agcacggtgc acatcgctcc   2880
ctcgtctcgc ctgccctacc ctgagttccg caagaatgtg ctcctccgca gcaccatgtt   2940
tgtgggcggc cgcctgggca gcttcagccc cagccgctgc tcctacagct acagctccct   3000
ggtggtggac gagcagtcct accggggtct gagtgtgacc tgctgcttcg atcagacctg   3060
tgagatgtac aagctgctgc agtgtacgga ggcggacgag atggagacgg ataccctctca   3120 gcagtacgcc tgcctgtgcg gggacaatca cccctggccg caggtgcggc agatgaaagt   3180
gacagacgcg ctgcgggccc cccggtccct ggtgagctgc aactgggggg agttcagcga   3240
tgacgatgac tgaggatgag tcacccccctc ccctcctctt gcaggtacgt ggccccgccc   3300
agtgggatgg gctttggatg ggggagggggt gttccctata aaggggggat gggggtggag   3360
gcatgcagcc ccacgggggaa gcttgtgtgg aggatgtctt ccgagggtga gatccggacc   3420
tgcttcattt cagctcgtct tcccagctgg gccggcgtgc gtcagggagt ggccgggacg   3480
```

```
aatgtgaacg gcggagtggt gggcgcccct gcccagagcg gggtgctggc ctactcccgc    3540
ttcgttcagc agcaacagca gcagccgggg acggcggcga cggggtctgt gttccgggcg    3600
gtgtttccat cggtggatct gagcgcggag gtgggcatga tgcggcaggc gctggcggag    3660
ctgcggcagc agctgcagga gctgcgggag gtggtggaga tacagctgcg ggccacggcc    3720
tcggaggcgg ccgaggagga agaggaggag gagattgtgg tggacgagga ggtggcgccc    3780
ggcgctggag cgaacaccat ggaagaggag gaggatgaga tggtcctgac gatgactgtg    3840 gtggggacc ctgagcctgc tggagtggaa gcccagccgc caccaccacc caccccggag     3900
agcgaccctg cggtgcctgc tactaccact accccgaagc ggctcagcta cggcgcgagc    3960
aagaggagcg gtccatgcgc ggaggacaac tgacgcggac tgtgggggga agaaggggga    4020
ggaggaaaga agaccatgga gacgggtgtt tgtctttttc cagcccaact ttattgagaa    4080
taataataaa gcttatggat gtttggaacg ataatagcgt gtccagcgtt ctctgtcttg    4140
cagggtcttg tgtatcttct cgaggcaccg gtagacctgg tgttggacgt tgaaatacat    4200
gggcatgact ccctcggcgg ggtgcaggta aagccactgg agggctgggt gcggggggca    4260
ggtgcagtag atgatccagt cataggcgtt ctggttgcgg tggtggttga aaatgtcctt    4320
gaggagcagg ctgatggcgg tgggcagacc cttggtgtag gcattgatga accggttgac    4380
ctgggcgggc tgcatgaggg gggacatgat gtggtacttg gcctggatct tgaggttgga    4440
gatgttgccg ctctggtcgc ggcgggggtt catgttgtgg aggacgacga ggacggcgta    4500
gccggtgcag cggggggaagc gggcgtgcag cttggagggg aaggcgtgga agaacttggc    4560
gacccccttg tgtccgccga ggtcctccat gcactcgtcg aggacgatgg cgatgggtcc    4620 gcggcggcg gcgcgggcga agacgttgcg tgagtcagtg acatcatagt tgtgctcctg     4680
catgaggtcc tggtagctca tgcggacaaa gtctggcatg agggtggcgg tctgggggat    4740
tagggtgtgg tccggaccgc tgcggtagtt gccctcgcag atctggtct cccaggcgac     4800 tacctcctgc gggggatca tgtccacctg cggggtgatg aagaaaacag tctccggcgg     4860
gggggagagg agttgggagg agatgaggtt gcggagcagc tgggacttgc cggagccggt    4920
gggaccgtag atgacagcga tgactggctg gacctggtag ttgagggagc ggcaggtgcc    4980
agccggggtg aggaagggca tgcaggcgtt gagggtgtcg cgcaggttgc ggttctcttg    5040
gacgaggtcc tgcaggaggt gtcggcctcc cagggagagg aggtgggaga gggaggcgaa    5100
ggccttgagg ggcttgaggc cctcggcgta gggcatgtcc tgcagggcct ggtggagcac    5160
gcgcatgcgc tcccagagct cggttacatg tcccacggta tcgtcctcca gcaggtctgg    5220
ttgtttctcg ggttgggqtt gctgcgtgag tacggaacga ggcggtgggc gtcgagcggg    5280
tggagggtcc ggtccttcca gggccggagg gcccgcgtga gggtggtctc ggtgacggtg    5340 aaggggggcgg tctggggctg ctcggtggcc aggtcctct tgaggctgag gcggctggtg    5400
ctgaaggtgg cgcttccgag ctgcgcgtcg ttcaggtagc actggcggag gaggtcatag    5460
gagaggtgtt gggtggcatg gcccttggcg cggagcttgc cggggccgcg gtgcccgcaa    5520
gcatcgcaaa cggtgtcgcg cagggcgtag agcttggggg cgagcaggac cgtctcggag    5580
ctgtgggcgt cgctgcggca gcgctcgcac tgggtctcgc actcgaccag ccaggtgagc    5640
tgggggttct gggatcgaa gacgagggg ccccgttcc gcttgaggcg gtgtttacct       5700
ttggtctcca tgagctcgcg tccggcgcgg gtgaggaaga ggctgtcggt gtcccgtag     5760 acggagcgca gggccggtc ggcgatgggg gtgccgcgt cgtcggcgta gaggatgagg      5820
gcccactcgg agatgaaggc acgcgcccag gcgaggacga agctggcgac ctgcgagggg    5880
```

-continued

| | | | | |
|---|---|---|---|---|
| tagcggtcgt | tgggcactaa | tggcgaggcc | tgctcgagcg | tgtggagaca gaggtcctcg | 5940 |
| tcgtccgcgt | ccaggaagtg | gattggtcgc | cagtggtagt | ccacgtgacc ggcttgcggg | 6000 |
| tcgggggta | taaaaggcgc | gggccggggt | gcgtggccgt | cagttgcttc gcaggcctcg | 6060 |
| tcaccggagt | ccgcgtctcc | ggcgtctcgc | gctgcggctg | catctgtggt cccggagtct | 6120 |
| tcaggtgggt | acgctacgac | aaagtccggg | gtgacctcag | cgctgaggtt gtctgtttct | 6180 |
| atgaaggcgg | aggagcggac | ggagaggtcg | ccgcgggcga | tggcttcggt ggtgcgggcg | 6240 |
| tccatctggc | tggcgaagac | caccttctta | ttgtcgaggc | gtgtggcgaa actgccgtag | 6300 |
| agggcgttgg | agagaagctt | ggcgatgctg | cggagcgttt | ggtttctgtc ccggtcggcc | 6360 |
| ttttccttgg | cagcgatgtt | gagctgcacg | tagtctcggg | cgaggcagcg ccactcgggg | 6420 |
| aagatgctgt | tgcgctcgtc | cggcaggagg | cgcacggccc | agccacggtt gtggagggtg | 6480 |
| accacgtcca | cggaggtggc | tacctcgccg | cggaggggct | cgttggtcca gcagaggcgg | 6540 |
| ccgcccttgc | gggagcagta | gggggcagg | acgtccagct | ggtcctcgtc gggggggtcg | 6600 |
| gcgtcgatgg | tgaagagggc | gggcaggagg | tcgggtcga | agtagctgag gggctcgggg | 6660 |
| ccgtcgagcc | ggtcctgcca | gcggcgggcg | gccaggcgc | ggtcgaaggg gttgaggggt | 6720 |
| tggccggcgg | ggaaggggtg | ggtgagggcg | ctggcataca | tgccgcagat gtcatagacg | 6780 |
| tagaggggct | cccgcaggag | gccgatgaag | ttggggtagc | agcggccgcc gcgcaggctc | 6840 |
| ttcgcggacg | tagtcataca | gctcgtggga | gggcgcgagg | aggttcggcc gaggtgcggc | 6900 |
| gcctggggcc | ggctggcgcg | gtagaggagc | tgcttgaaga | tggcgtggga gttggagctg | 6960 |
| atggtgggcc | tctggaagac | attgaaggcg | gcgtggggaa | ggccggcctg cgtgtggacg | 7020 |
| aaggcgcggt | aggactcttg | cagcttgcgg | accagacggg | cggtgacgac gacgtcctgg | 7080 |
| gcgcagtagc | gcaggtggc | ctggacgatg | tcgtaagcgt | cccctggct ctccttcttc | 7140 |
| cacaggtcct | tgttgaggag | gtactcctga | tcgctgtccc | agtacttggc gtgtgggaag | 7200 |
| ccgtcctgat | cgcgtaagta | gtccccgtg | cggtagaact | cgttcacggc atcgtagggg | 7260 |
| cagtgtccct | tgtccacggc | cagctcgtag | gccgcggcgg | ccttgcggag gctggtgtgc | 7320 |
| gtgagggcga | aggtgtcccg | gaccatgaac | ttgacgtact | ggtgctgggg gtcctcgggg | 7380 |
| gccatgacgc | cctcctccca | gtccgcgtag | tcgcggcgcg | ggcggaaggc ggggttgggc | 7440 |
| aggttgaagc | tgatgtcatt | gaagaggatg | cggccgttgc | gcggcatgaa ggtgcgggtg | 7500 |
| accaggaagg | agggggcac | ctcgcggcg | tgggcgagca | cctgcgcggc caggacgatc | 7560 |
| tcatcgaagc | ccgagatgtt | gtggcccacg | atgtagacct | ccaggaagag gggcggcccg | 7620 |
| cgcaggcggc | ggcgccgcag | ctgggcatag | gccaggggt | cctcggggtc gtccggcagg | 7680 |
| ccggggcccc | gctcctgcgc | cagctcggcg | aggtctgggt | tgtgggccag caggtgctgc | 7740 |
| cagagggtgt | cggtgaggcg | ggcctgcagg | gcgtgccgca | gggccttgaa ggcgcggccg | 7800 |
| atggcgcgct | tctgcgggca | gagcatgtag | aaggtgtggg | ctcgggtctc cagcgctgca | 7860 |
| ggcgggctct | ggacggccac | cacctgcagc | gcggcgtcca | gcagctcctc gtccccgag | 7920 |
| aggtggaaga | ccagcaggaa | gggcacgagc | tgctttccga | agcggccgtg ccaggtgtag | 7980 |
| gtctccaggt | cataggtgag | gaagaggcg | cgggtgccct | cggggagcc gatgggcgg | 8040 |
| aaggcgatgg | tctgccacca | gtcggccgtc | tggcgctgaa | cgtggtggaa gtagaagtcc | 8100 |
| cggcggcgca | cggagcaggt | gtgggcggtc | tggaagatgc | ggccgcagtg ctcgcacttc | 8160 |
| tgggcctcct | ggatgctctt | gatgaggtgg | cagcggccct | gggtgaagag caggcggagg | 8220 |
| gggaaggga | ggcggggcgg | cgggccctcg | gcgggggt | cccagcgcac gtggtgcagg | 8280 |

-continued

```
tggtgttgct ggcgggtgac cacctggacg aaggtgggcc cggcggcgcg ggccagctcc    8340
accgcggtct gggggtagc ctgcaggagg tcggggggcg ggcgcaggag gtgcagctgg     8400
aagaggttgg ccagggcgct gtcccagtgg cggtggtagg tgatgctcca gctctccccg    8460
tcctgggtgg tgccctggag gcggagggtg gcgcggcgct cgagcaggag cccccgcgtg    8520
ccggcctccg cggcctcggc ggcggcggcc ggtctcaggc gggcagctgg gccaggggca    8580
cgggcgcgtt gagctcgggc agcgggaggt ggtcgcggcg cagacgcgag gcgtgggcga    8640
tgacgcggcg gttgatgttc tggatctgcg ggttcccgga aagaccacg ggcccggtga     8700 ctcggaacct gaaagagagt tccacggaat caatgtcggc atcgtgggtg ccacctggc     8760 gcaggatctc ggacacgtcc ccgctgtttt cgcggtaggc gatgtcctgc atgaactgct    8820
cgagctcgtc ctcgtccagg tccccgtggc cggcgcgctc caccggtggcg ccaggtcga    8880 cggtgatgcg gttcatgatg ccaccaggg cgttctctcc gttctcgttc cacacgcgac     8940
tgtagaccag ctggccgtcg gcgtcccgcg cgcgcatgac tacctgggcc aggttgagcg    9000
ccaccaggcg gttgaagggc gcctgcaggc gcagggcgtg gtgcaggtag ttgagggtgg    9060
tggcgatgtg ctcgcagagg aagaagttta tgacccagcg gcgcagggtc agctcgttga    9120
tgtcgcccag gtcctcgagg cgctgcatga cccggtagaa ctcggggggcg aagcgaaaaa    9180 actcgtgctg gcgggccgag accgtgagct cctcttccag ggcggcgatg gcctcggcca    9240
ccgcctgccg cacctcctcc tctaaggagg gcgggggcgt gctgggtccg gccaccgccg    9300
cctcttcttc ctcttctccc tccagggggtg gcatctcctc gtcttcttct tctgctgctg    9360
ctgcctccgc ggggacgggg ggcgcaggcc ggggacggcg ccggcgcaag ggcagccggt    9420
ccacgaagcg ctcgatgacc tcgccccgca tgcggcgcat ggtctcggtg acggcgcggc    9480
cgccctcccg gggccgcagc tcgaaggcgc ccccgcgcag cgcggtgccg ctgcagaggg    9540
gcaggctgag cgcactgatg atgcagcgtg tcaactctct cgtaggtacc tcctgctgtt    9600
gcagcgcttc ggcaaactcg cgcacctgct cttcggaccc ggcgaagcgt tcgacgaagg    9660
cgtctagcca gcaacagtcg caaggtaagt tgagcgcggt gtgcgtcggg agccggaggt    9720
gccggctgac gaggaagtga agtaggccg tcttgagctg ccggatggcg cgcaggaggg     9780 tgaggtctttt gcggccggcg cgctgcaggc ggatgcggtc ggccatgccc caggcctcct    9840
gctggcagcg gccgatgtcc ttgagctgct cctgcagcag atgtgccacg ggcacgtccc    9900
ggtcggcgtc caggtgggtg cgaccgtagc cccgcagggg gcgcagcagc gccaggtcgg    9960
ccaccacgcg ctcggccagg atggcctgct gcatgcgctg cagggagtct gagaagtcat   10020
ccaggtccag gaaccggtgg taggcgcccg tgttgatggt gtaggagcag ttgcccagca   10080
cggaccagtt gaccacctgg tagtgggct ggatgacctc ggtgtagcgc agtcgactgt    10140
aggcgcgcgt gtcaaagatg taatcgttgc agaggcgcag caggtgctgg tagcccacga   10200
gcaggtgggg cggagggtag aggtagaggg gccagtgttc cgtggccggt tggcggggggg   10260 agaggttcat gagcatgagg cggtggtagc ggtagatgaa gcgggacatc caggcgatgc   10320
cgacggcgga gacggaggcg cgggtccact ggtgggcgcg gttccaaatg ttgcgcaccg   10380
ggcggaagag ctccacggtg taaatggatt gccccgtgag gcgggcgcag tcgagggcgc   10440
tctgtcaaaa agaaccgggt gtggttggtt ggtgtgtggt agcgatctat ctttctttgt   10500
gatcttggta gtgaagcctg ccaggctcca gcagggggcg tccgccgtct tccttccttt   10560
ccctatctgg aggtgtgtct ctgttctctt ttttatttca tgtagccatg catcccgttc   10620
tgcggcagat gaagccgccg gccggcgccc tgggcgcgga ggggcgacg cgctctcggt    10680
```

```
cgccctcgcc gtcgctgacg cggccgcgcg aggaggggga gggcctggcg cggctgtcgg    10740
gcgcggcggc ccccgagcgg cacccacggg tgcagctcaa gcgagaggcc atggaggcct    10800
atgtgccgag gcagaatgcg ttccgcgagc gaccggggga ggagggggag gagatgaggg    10860
acctgcggtt ccgcgcgggg cgggagatgc agctggaccg ggagcgagtg ctccagcccg    10920
aggactttga ggggcgcgtg gaggaggcgg ggggagtgag cgcggcgcgg cccacatga    10980
gcgcggccag cctggcccag gcctacgagc agacggtacg cgaggaggtc aacttccaaa    11040
agaccttcaa caacaacgtg cgcaccctgg tgagccggga cgaggtgacc atgggactga    11100
tgcacctgtg ggactttgtg gaggccttcc tgcagcaccc ccggtcccgc gcgctgaccg    11160
cgcagctgct gctgatcgcg cagcactgcc gggacgaggg catggtgaag gaggcgctgc    11220
tgagcctggg cgcgcccgag agccgctggc tggtggacct ggtgaacctg ctccagacca    11280
ttgtggtgca ggagcggtcc atgagcctga gcgagaaggt ggcggccatc aactactcgg    11340
tggcgaccct ggccaagcac tacgcgcgca agatctccac cttctacatg cgcgcggtgg    11400
tgaagctgct ggtgctggcc gacaacctgg gcatgtaccg caacaagcgg ctggagcgcg    11460
tggtcagcac ctcgcggcgg cgcgagctca atgacaagga agctcatgtt tggcctccgc    11520
cgggcgctgg ccggggaggg cgaggaggac ctggaggagg aggaggacct ggaggaggcg    11580
gaggaggagg agctggaaag aggaggagtt cggtccccgg ggaccgcggc gcgtgaggtg    11640
gcagtccccg ctgactgcga gcgatgaggg tgatgtgtac tgatggcaac catccccctt    11700
tttaacaaca acagcagcat ggcggcgagc tctgaagctg gggcggcggc ggcggggtg    11760
agcgcggcct ccctggcgcc cgagcgggcg acgcggatgc aggcgctgcc ctccctggac    11820
gagccttggg agcaggctct gcggcgcatc atggcgctga cggccgacgg gtctcggcgc    11880
ttcgcgagcc agcccctggc caaccgcatc ggggccatcc tggaggcggt ggtgcctccg    11940
cgcacgaacc cgacgcacga gaaggtgctg accgtggtga acgcgctgct ggagacctcg    12000
gccatccgcc cggacgaggc cggcatggtg tacgatgcgc tgctggagcg ggtctcccgc    12060
tacaacagcg gcaacgtgca gaccaacctg gaccggctgt cccaggacgt gcggcaggtg    12120
atcgcccagc gcgagcgctc gagcgccaac aacctgggca gcctggccgc gctgaatgcc    12180
ttcatcgcct cgctgcccgc aacggtggag cggggccagg agagctacct ggggttcctc    12240
agcgcgctgc ggctgctggt gagcgaggtg ccgcagacgg aggtgttccg ctcggggccg    12300
cacaccttcc tgcaggcggc gcggaacggt tccaagacgg tgaacctcaa ccaggccatg    12360
gagaacctgc ggcccctgtg ggggctgcag gcccccgctg gggagcgcgg gcacgtgtcc    12420
tccctgctga cgcccaacac ccggctgctg ctgctcctgg tggctccctt cgcggaggag    12480
atgaacgtca gccggagctc ctacattggg cacctgctga cactctaccg cgagacgctg    12540
gccaacttgc atgtggacga gcgcacgtac caggagatca ccagcgtcag ccgggcgttg    12600
ggcgacgagg acgacgcggc gcggctgcag gccaccctca acttcttcct gaccaaccgg    12660
cagcggcggc tgccggcggc gtatgccctg accgccgagg aggagcgcat cctgcgctac    12720
gtgcagcagg ccgtgagcct gtacctgatg caggacgggg cgacgccac gggcgccctg    12780
gacgaggcca gccgcaacct ggagcccagc ttctacgcgg cgcaccggga cttcatcaac    12840
cgcctgatgg actacttcca tcgcgcggcc gcggtggcgc ccaactactt tatgaatgcc    12900
gtcctgaacc ccgctggct gccctcggag ggcttcttca ccggcgtgta tgacttcccg    12960
gagcaggacg agggggagga gcggccctgg gacgcctttg acagcgacga ggagggccgc    13020
ctcatgctgc ggtccgcagc ctcctcagag ccctcctcct ccttcacccc cctgccctg    13080
```

-continued

```
accgaggagc cgccctcgcg gccctccacc ccggccctct cgcgcgtccc gtcccgggca    13140
tcctccctgc tctctctggc ctctctggga aagcgggagg gagggactc gctcgcctac     13200 tcgccggcca cgcccaccta tggctctcgc tggggctcgc gccgctccag cctggccagc    13260
ggcgccgaca gcctggagtg ggacgcgctg ctggccctc ccaaggatgt gaacgagcac     13320
ccaggcgccg ccgccggccg ccgccgccgc gcctcccgct cctccctgga ggaggacatc    13380
gacgccatca gcagccggct gttcacctgg cgcacgcgcg cccaggagat gggcctgccc    13440
gtggccagct ctcccgcccg ccaccagccg cgccccgggg ccctcgaaga cgacgaggag    13500
gaggaagact ggcgccagga ccggttcttt cgcttcgaag cgcccgagga aaacccttc    13560 cgccacatcg cccccaaggg gctgtaatgc aaaaagcaa aataaaaaac ccctcccggt     13620
ccaactcacc acggccatgg ttgtccttgt gtgcccgtca gatgaggagg atgatgccag    13680
cagcgccgcc gcaggagcg tcgcctccgc cgtcctacga gagtgtggtg gggtcttcgc    13740
tcacggagcc tctttatgtg ccgccgcggt acctgggccc caccgagggg cggaacagca    13800
tccgttattc acagctcccg ccgctctacg ataccacaaa gatctatctg atcgataaca    13860
agtcggcgga tatcgccagt ctgaactacc aaaacaacca cagtgacttt ctcaccagcg    13920
tggtgcagaa cagcgacttc acgcccatgg aggcgagcac gcagaccatc aacctggatg    13980
agcgctcgcg ctggggcggg gagtttaaga gcattctgac caccaacatc cccaacgtga    14040
cccagtacat gttcagcaac agcttccggg tgcgcctgat gagcgcgcgc gataaagaga    14100
caaatgcccc cacctacgag tggttcaccc tgacccctgcc cgagggcaac ttctcggaca   14160
tcgcggtcat cgacctgatg aacaacgcga tcgtggagaa ctacctggcg gtggggcggc    14220 agcaggggt caaggaggag gacatcgggg tgaagatcga cacgcgcaac ttccgcctgg    14280
gctatgaccc ggagaccaag ctggtcatgc ccggcagcta caccaacatg gcctttcacc    14340
ccgacgtggt gctggcaccg ggctgcgcca tcgacttcac cttctcccgc ctaaacaacc    14400
tgctgggcat ccgcaagcgc taccccctacc aggagggctt catgctgacc tacgaggacc    14460
tggcgggggg caacatcccc gcgctgctgg acctcaccac ctatgatcag gagaactcca    14520
gcaccatcaa gcccctgaag caggacagca agggtcgcag ctaccacgtg ggcgaggacc    14580
ccgaggcggg ggacaccttc acctactacc gcagctggta cctggcctac aactacgggg    14640
acccggccac gggcaccgcc tcccagacgc tgctggtctc cccggacgta acctgcggag    14700
tggagcaggt ctactggagc ctgccggacc tgatgcagga cccggtgacc ttccggccca    14760
gccagacgcc gagcaactac ccggtggtag ccacggagct actgccgctg cgctcccggg    14820
ccttctacaa cacccaggcc gtgtactccc agctcctgca gcaggccacc aacaacaccc    14880
tggtctttaa ccgcttcccg gagaaccaga tcctcctgcg cccgccagag tccaccatca    14940
cctccatcag cgagaacgtg ccctcgctga cggaccacgg cacgctgccg ctgcgtaaca    15000
gcatccccgg ggtgcagcgg gtaaccgtca ccgacgcgcg gcgccgcgtg tgtccctatg    15060
tgtacaagag tctcggggtg gtgaccccga gggtgctcag cagccgaacc ttctaaccga    15120
cagccctacc cgtcacaggg gagacagaga aagacagcc agccccgcca tggccatcct    15180
cgtctcgccc agcaacaact ttggctgggg actgggcctg cgctccatgt acggggcgc    15240 ccgccgcctg tccccggatc acccccgtgat cgtccgacgc cactaccggg ccaactgggc    15300
cagtctgaag ggacgcgtgg cccccagcac catagcgaca acggatgacc ctgtggccga    15360
cgtggtcaac gcgatcgccg gcgccaccccg ccgccggcgc cgccatcgtc gacgtcgag    15420 ggccgcgcgc gtctcctccg tggccgtcac cggggacccg gtggccgatg tggtcaacgc    15480
```

```
ggtggaggcg gtagcccggc gccgccgcgc gcggcgccgt tcttcgcgca tgcagaccac    15540
gggggacccc gtggcggatg tggtggcggc ggtggaagcg gtggcgcgcc ggaggcggag    15600
caccCggcgg cggcgcaggc gctccgcgcc ggccatcctg ggggtgcgcc gcagccgccg    15660
cctccgcaaa cgcacctcgt cctgagattt ttgtgttttg ttttttctgc ctcccgtggg    15720
tgaacaagtc catccatcca tccaacatcc gtggctgctg tgtctttgtc ttttctttgc    15780
gttgcgcccc agttgagccg gcaccgacgc gctcggccat ggccatctcg cgccgcgtga    15840
aaaaggagct gctgcaggcg ttggcgcccg aggtgtacgg ggcgcctaag aaggaggaga    15900
aggacgtcaa agaggagtcc aaagctgacc ttaaaccgct gaagaagcgg cgcaaggcca    15960
agcgggggtt gagcgacagc gacgaggtgc tggtgctggg cacgcgcccc aggcgccgct    16020
ggacggggcg gcgcgtgcgc gcccacctac cgcccggtgc cagcctcgcc tacgtcccgg    16080
gtcttcggag gtcgagcgcc accaagcgct ctgcggacga gttgtatgcg gacacggaca    16140
tcctgcagca ggcgtcccag cgcctgaacg aatttgctta tggcaagaga gcccggcggc    16200
agcggcgggc ccgcccctcg ccgacccccg cgtcccgcgg ccggaccacc aagcgctctt    16260
atgacgaggt cgtggcagac agtgacatcc tgcagcaact ggatccgggg accgctcca    16320
atgagttctc ctatggcaag cggtcgctgc tgggggagtc aggagacacc gtcccggctg    16380
tggccgtccc gctggaggaa ggcaggaacc acacacccag cctgcagccg ctcaccgagc    16440
ccatgcccct ggtgtcccct cgcacggccg tcaagcgccg ggcgcccgcc gacgagccca    16500
ccgcctcact ggtccccacc gtgcaggtcc tggcccccaa gcgtcgtctg caggaggtgg    16560
tggtggagcc gcccgctcca gcacccacgc cgccctagc cccgcggcgg tccagccggc    16620
gcatcattct ggctccgcgc cgggcggcc ggccccaggc cgtcgtggcg ccgcagctca    16680
gcgcggccgc ggcgctggag cgggcggcgg ccgccgtgcc cctgccaccg gacacggagg    16740
acgacctggt ggagatggca gaggctgtcg ccgcgcccga ggtgctgccc agcctccccg    16800
tctccatcat gccgcccacc gccacggagg tggccctgcc cgtacagacc ccactgccgc    16860
ccgtggcggt ggccaagagc tccctgaccc ccggcctccg cgcgctgatg ggcaccgagc    16920
gggtgccggt tccagtcctg gaggcgcccc tggtggccat gcccgtgctc cgggccacca    16980
ccgcccgtgc cgagccccg cgccgcgtgc cccgcagggc cgtgcgggac atccggggca    17040
ggcagccccg cacggtatcc ctgcccgtgc tcacggagcc cggcccggcc accgcggtcg    17100
cctccgtgcg cgcggcagcc caagtcctgc aggcgccccc cgcccgaccg gccaccgtct    17160
ccgtgggggt gggcaccgag ccggtggtgc agtccatcac ggtcaagcgg tcaaagcgcc    17220
tgaccaagca ccatcggggt gcagaccatc gacgtcaccg tgcccaccgt ccgcactgtc    17280
agcgtgggca ccaacacgcc ccggctgagg agcgcctcgg tgggcgtcca gaccgctccc    17340
gagacccgct cccaggggt gcaggtggct ttccaaccag cgtgctagcc caccgcacac    17400
ccaggcaggt gcggctgacg gcggtggtgc cccccacccc gcgcgcccg gtggttccgg    17460
tggcccggcg cccgcggcgg ttccggtgcc tccccagcc cctccagccc cgcgcgcgcc    17520
gcgtgcgcct cgcgccccca gagcgcctcg cgtcgccgc cgtaccccgg tggcggtggc    17580
agcgccgccc gcccgcagcg gcggtccccc ggcctcggct gccgaggcgg cccatcgtgc    17640
tgcccggggt gcgctatcat cccagtcagg ccatggctcc caccgcccaa cgcgtcatct    17700
ggcgttgatt tatttttgga gacctgactg tgttgtgttc cttaaatttt ttatcctcct    17760
cctcctctgc tgaagccaga cgatgctgac ctaccggttg cggctgcccg tgcggatgcg    17820
gagaccgaga ctccgcggtg ggttccgcgt ggcgcctcgg cgcagcggcg gcaggcggcg    17880
```

```
gtaccgccgg gggccgatga ggggtggcat cctgccggcg ctggtgccca tcatcgcggc    17940
atccatctgg gccatccccg gcatcgcctc ggtggcgatg agtgctagac aacgcaatta    18000
acggcgctgc tgtgtatgtg tgtcttccat gtgccttcct tccttcgttc ccaacggaac    18060
agcagcaccg tctccatgga ggacctaagc ttttccgcgt tggctccacg ctttggcacg    18120
cggccggtca tgggcacttg gagcgaaatc ggcacgagtc agatgaacgg cggcgcgctc    18180
agctggagca atatctggag cgggctgaag agctttggta gttctctggc ctccacggcc    18240
aacaaggcct ggaacagcgg gacggtgacg agcgtgcgca acaagttgaa ggatgccgac    18300
gtgcagggga agataggtga ggtcattgcc tccggggtcc acggtgccct ggacgtggcc    18360
aaccaggccg tctcccacgc cgtggaccgc cggtgcaaca gcagcagctg cggcagcagc    18420
agctcctccg ccagcagcag caacagatgg gcctcgtgga accctcctat gagatggaga    18480
cagacgagct gcctcctccc cccgaggacc tcttgcctcc tcctcctcct ccgccgcctg    18540
cctcggccac tcccgcgcgc caatcccgcg ggacgtcccg ccaagcgccc gccgccgccc    18600
aggagatcat catccgctcc gacgagcccc ctccctatga agagctgtat cccgacaagg    18660
ccgggatccc cgccaccttg gagctgcgtc ccgagaccaa actgcccgcc gtggcccaca    18720
ataagatgcg ccccccgccg ccgctcacca ccaccacctc ctccgctgcc gccgccgccc    18780 ccgcccggc ccccgcggct cctgtgcgtc ggcgtccggc cgcggctccg gccgcggctc    18840
cggcgagttc caaaggcccc ccaggtgggg gtccgcgcgc gcgggtggca aaacaaactc    18900
aacaccattg tgggactggg tgtccgcaca tgcaagcgcc gtcgttgtta ctgagagaga    18960
cagcatggag aaacaacaat gtctggattc aaataaagac acgcctattc ttccacggtg    19020
ctccgcgctg tgttattttc aacgggctgt ttccttttgc atctctgtgc catcgcgcca    19080
cggggaattc cgcaggatgg cgacgccgtc gatgatgccg cagtggtcct atatgcacat    19140
ctccgggcag gacgcgtccg agtacctgtc tcccgggctg gtgcagttct cccaggcgac    19200
ggagacctac tttaacctga caacaagtt taggaacccc accgtcgcgc ccacccacga    19260
tgtgacgacg gagcgctcgc agcggctgca gctgcgcttc gtccccgtgg acaaggagga    19320
cactcagtac acatacaaga cccgcttcca gctggcggtg ggcgacaacc gcgtgttgga    19380
catggcgagc accttctttg acatccgggg aacgctggac cggggaccct ccttcaaacc    19440
gtactcgggc accgcgtaca acatcatggc tcccaagagc gctcccaaca actgtcaata    19500
tctagaccct aaaggtgaaa ctgaggctgg caaagttaat accattgctc aagcaagttt    19560
tgtgggtcct attgatgaaa ccacgggaga cattaaaatt acagaagaag aagacgaaga    19620
gaccaccatc gatcctttgt atgagcccca accccagctt ggtccaagct cgtggtcaga    19680
caatatacct tctgcgacta gcggagctgg aagagttctc aaacagacca caccgcgtca    19740
accttgttac ggttcttatg cctctccgac aaatattcac ggtgggcaaa cgaaggatga    19800
caaggttaca ccattgtact ttacaaacaa tcccgccacc gaagccgaag cactcgaaga    19860
aaatggatta aagccaaatg tcaccctata ctcagaggat gttgacctaa agcaccaga    19920 tactcatctg gtctatgctg tgaatcaaac ccaggaattc gctcaatatg acttggaca    19980 acaggccgct ccaaacaggg ccaattacat cggcttcagg acaactttta tcgggctgtt    20040
gtactacaac agcaatggca accagggcat gctagccggt caggcctctc agctcaacgc    20100
ggtggtcgac ctgcaggaca ggaatcaccg aactagctac cagctcttcc tcgatagcct    20160
ctatgacagg tcgaggtact ttagcctgtg gaaccaggcc atcgattctt atgacaagga    20220
tgtgcgtgtg ctggaaaaca atggcgtgga ggacgagatg cccaactttt gctttcccat    20280
```

```
cggcgccatc gagaccaaca tgacatttac acagctcaaa aagagtgaga atggtggctc    20340
aagagccaca acctggacaa aggagaatgg ggatgatggc ggaaacggag cggagcacta    20400
cctgggcatc ggcaacctca acgccatgga gatcaatctc acggccaacc tctggcgcag    20460
cttcctctac agcaacgtgg cgctgtacct gcctgacaag tacaagtttt ccccgcccaa    20520
cgtccccatc gaccccaaca cgcactccta tgactacatc aacaagcgcc tgcccctcaa    20580
caacctcatt gatacctttg tcaacatcgg ggcgcgctgg tccccggatg tcatggacaa    20640
cgtcaacccc ttcaaccacc accgcaacta cggcctgcgc taccgctccc agctcctggg    20700
caacggccgc tactgcaagt tccacatcca ggtgccgcaa aagttctttg ccctcaagag    20760
cctgctgctc ctgccggggg cgacctacac ctacgagtgg tccttccgca aggacgtcaa    20820
catgatcctc cagtccacgc tgggcaacga cctccgcgcg gacggggcca aaatcaacat    20880
cgagagcgtc aacctctacg ccagcttctt tcccatggcc cacaacaccg cctccaccct    20940
ggaggccatg ctgcgcaacg acaccaacaa ccaaaccttt attgacttcc tctcctccgc    21000
caacatgctc tacccccatcc cggccaacgt caccaacctg cccatctcca ttcccagccg    21060
caactgggcc gccttccgcg gctggagctt cacgcggctg aagcacaacg agaccccgc    21120 cctgggctcg cccttcgacc cctactttac ctactcgggc tccatcccct acctggacgg    21180
gaccttctac ctgggccaca ccttccgccg catcagcatc cagttcgact cctccgtggc    21240
ctggccgggc aatgaccgcc tgctcactcc caacgagttc gaggtcaagc gcaccgtgga    21300
cggggagggc tacacggtgg cccagaccaa catgaccaaa gactggttcc tggtgcagat    21360
gctcgcccac tacaacatcg gctaccaggg ataccacctg ccagagggct accgcgaccg    21420
cacctactcc ttcctgcgca actttgagcc catgtgccgc caggtgcccg actacgccaa    21480
ccacaaagat gagtacctgg aggtgcccac caccaaccag ttcaacagca gcggctttgt    21540
atccgcggcc ttcaccgccg gcatgcgcga ggggcaccca taccccgcca actggccta    21600 cccgctcatc ggcgaagacg ccgtgcagac cgtgacccag cgcaagttcc tctgcgaccg    21660
cacgctctgg cgcatcccct ctcctccaa cttcatgtcc atgggcaccc tcaccgacct    21720
gggccagaac ctcctctacg ccaactcggc ccacgccctc gacatgacct tcgaggtcga    21780
cgccatggat gaaccccaccc tctttgtatgt tctgttcgag gtctttgacg tctgcggcgt    21840
gcaccagccg caccgaggcg tcatcgaggc cgtctacctg cgcacgccct ctccgccgg    21900 gaacgccacc acctaaggcg gagccgcgca ggcatgggca gcaccgagga cgagctccga    21960
gccatggcgc gcgacctcca gctgcccgc ttcctgggca cctttgacaa gtccttcccg    22020
ggcttcttgc aagagtccca gcgctgctgc gccatcgtca acacggccgc ccgccacacc    22080
ggaggccgcc actggctggc cgtcgcctgg gagcccgcct cgcgcacctt ctacttcttt    22140
gacccctccg gcttctccga ccgggagctc gcccaggtct atgactttga gtaccagcgc    22200
ctgctgcgca agagcgccat ccagagcacc ccggaccgct gcctcacgct cgtcaagagc    22260
acccagagcg tgcagggacc gcacagcgcc gcctgcggac tcttctgcct cctcttcctc    22320
gccgcctttg cccgctaccc cgacagcccc atggcctaca atcccgtcat ggacctggtg    22380
gagggcgtgg acaacgagcg gctcttcgac gccgacgtcc agcccatctt ccgcgccaac    22440
caggaggcct gctacgcgtt cctcgctcgc cactccgcct acttccgcgc ccaccgccac    22500
gccatcatgg aacagacaca cctgcacaaa gcgctcgata tgcaataaag ctttttatt    22560 gtaagtcaaa aaggcctctt ttatcctccg tcgcctgggg gtgtatgtag atgggggac    22620 taggtgaacc cggacccgcc gtcggctccc ctccatcccc tcttctctca aaacaggctc    22680
```

-continued

```
tcatcgtcgt cctccgttcc cacggggaag atggtgttct gcacctggaa ctggggcccc    22740
cacttgaact cgggcaccgt cagtggaggc cgcgtctgca tcagggcggc ccacatctgt    22800
ttggtcagct gcagggccag catcacatcg ggggcgctga tcttgaaatc acaattcttc    22860
tgggggttgc cgcgcgaccc gcggtacacc gggttgtagc actggaacac cagcaccgcg    22920
gggtgggtca cgctggccag aatcttgggg tcttccacca gctgggggtt cagcgccgcc    22980
gacccgctca gcgcgaaggg ggtgatcttg caggtctgcc ggcccagcag gggcacctgg    23040
cggcagcccc agccgcagtc gcacaccagc ggcatcagca ggtgcgtctc cgcgttgccc    23100
atccgggggt agcaggcctt ctggaaagcc ttgagctgct cgaaggcctg ctgcgccttg    23160
gagccctccg agtagaagag gccgcaggac cgcgccgaga aggtgttggg ggccgacccc    23220
acgtcgtggc tgcaacacat ggccccgtcg ttgcgcagct gcaccacgtt gcggcccag    23280
cggttggtgg tgatcttggc gcgctcgggg gtctcgcgca gggcgcgctg cccgttctcg    23340
ctgttgagat ccatctccac cagctgctcc ttgttgatca tgggcagccc gtgcaggcag    23400
tgcagcccct ccgagccgct gcggtgctgc cagatcacgc acccgcaggg gttccactcg    23460
ggcgtcttca gacccgccgc cttcaccaca aagtccagca ggaagcgggc catcactgtc    23520
agcaggctct tttgcgtgct gaaggtcagc tggcagctga tcttgcgctc gttcagccag    23580
gcttgggccc cgcgccggaa gcactccagg gtgctgccgt ccggcagcag cgtcaggccc    23640
ttgacatcca ccttcagggg gaccagcatc tgcacagcca gatccatggc ccgctgccac    23700
ttctgctcct gagcatccag ctgcagcagc ggccgggcca ccgccgggct cggggtcacc    23760
gggcgcgggg ggcgggcccc ctcctcttcc tccccatctt cgcccttcct cctcgcgggc    23820
cgcgccgtcg ccgctgccgt tcttcagcc tcgtcctcct cctcctcgct gaccaggggc    23880
ttggcacgcg cgcgcttccg ccgctcctgc acgggcggag aggccgcgcg cttgcggcct    23940
cccccgcgcc ggctgggggt cgcgacagga gcgtcgtcca caatcagcac ccctcttcc    24000
ccgctgtcat agtcagacac gtccgaatag cggcgactca ttttgcttcc cctagatgga    24060
agaccagcac agcgcagcca gtgagctggg gtcctccgcg gccccgaccc ttccgccgcc    24120
accaccgccg ccacctccgc ccacgtcacc gccaccttca ctgcagcagc ggcagcagga    24180
gcccaccgaa accgatgacg cggaggacac ctgctcctcg tcctcctcgt cctccgcctc    24240
cagcgagtgc ttcgtctcgc cgctggaaga cacgagctcc gaggactcgg cggacacggt    24300
gctcccctcc gagccccgcc gggacgagga ggagcaggag gaggactcgc ccgaccgcta    24360
catgacgcg gacgtgctgc agcgccacct gctgcgccag agtaccatcc tgcgccaggt    24420
cctgcaggag gccgccccg gcgcagccgg ggaggccgcc gaggcgccct cggtggcgga    24480
gctcagccgc cgcctggaag cggccctctt ctcccccgcc acgccgccgc ggcgccagga    24540
gaacggaacc tgcgccccgg accccgcct caacttctac ccggtcttca tgctgcccga    24600
ggccctggcc acctacctcc tcttcttcca caaccaaaag atccccgtca gctgccgcgc    24660
caaccgccca cgagccgacg cgcactggcg gctgcccagt gggacccct tacctgacta    24720
tccaaccacc gacgaggttt acaagatctt tgagggcctg ggggacgagg agccggcctg    24780
cgccaaccag gacctgaaag agcgcgacag cgtgttagtc gagctcaagc tggacaaccc    24840
ccgcctggcg gtggtcaagc agtgcatcgc cgtcacccac ttcgcctacc cggccctggc    24900
gctgccaccc aaggtcatga gcacgctcat gcagaccctg ctggtgcgcc gcgcgagccc    24960
actcccgac gagggcgaga cgcccctcga ggacctcctg gtggtcagcg acagcagct    25020
ggcccgctgg atgcacacct cggaccccaa ggtcctggag gagcggcgca agaccgtcac    25080
```

```
cgccgcctgc atggtcacgg tgcagctcca ctgcatgcac accttcctca cctcccgcga    25140
gatggtgcgc cgcctcggag agtgcctcca ctacatgttc cgccagggct acgtcaagct    25200
agctagcaag atcgccaata tggaactctc taacctggtc tcctacttgg gcatgctgca    25260
cgaaaacagg ctcggtcagc acgtgctcca ccacaccctc aagcatgagg cgagacgcga    25320
ctacgtccgg gacaccattt acctatacct ggtctatacc tggcagaccg ccatgggggt    25380
ctggcagcag tgcctcgagg accgaaacct gcgcgccctg gaaacgtctc tggctcgcgc    25440
tcgccagagc ctgtggacgg gctttgatga gcgcactatc gcgcaggacc tcgccgcgtt    25500
cctttccccc accaagctcg tagagaccct gcagcgctcg ctccccgact tgccagcca    25560 gagcatgatg catgccttcc gctccttcgt cctcgagcgc tccggcatcc tgcccgccgt    25620
ctgcaacgcg ctcccctctg actttgtgcc caccgtctac cgcgagtgcc cgccgcccct    25680
ctgggctcac tgctacctcc tgcgcctcgc caacttcctc atgtaccact gcgacctcgc    25740
cgaggacacc tccggcgagg gcctctttga gtgctactgc cgctgcaacc tctgcgcacc    25800
gcaccgctgc ctcgccacca acaccgccct cctcaacgag gtgcaagcca tcaacacctt    25860
tgagctccag cggccccca agcccgacgg caccctgcca ccgcccttca agctgacccc    25920
cggtctctgg acctccgcct tcctccgcca ctttgtctcc gaggactacc actcggaccg    25980
catcctcttc tacgaggacg tgtcccgccc cccagggtg gagccctccg cctgcgtcat    26040
cacgcactcg gccattctcg cgcaattgca tgacatcaaa aaggccaggg aagagttttt    26100
gctgaccaaa ggccacggcg tctacctaga ccccccacac ggagaggagc tcaacaccgc    26160
cgccccgtcc accgccacc atgccgcccc tccggaggaa gcccatccgc agcagcacca    26220
gcaccagcag cagccgagcc accgcgccg ccaccaccgc tccagctacg cagaccgtgt    26280
ccgaagcgag ctccacgcct acggcggtgc gaccggttcc tcccgcgacc ctgtctctgg    26340
cggatgctct gccagaggaa cccactcccg cgatgctgct cgaagaagag gctctcagca    26400
gcgagaccag cggcagctcc gaaggcagtt tgctcagtac cctcgaggaa ctggaggagg    26460
aggaggaacc ggtcacaccg acgaggccat ccaagcccte ctacaccaac agcagcagca    26520
gcaagagcat cagccagcgc aggaactccg tcgtccccag cgaggctcgt agatggaatc    26580
agacatccat ccaccggagt agccagccag gtaggacacc tccgccctcg gcccgccgac    26640
gctcctggcg ccgctaccgc cacgacatcc tctcggccct ggagtactgc gccggagacg    26700
gagcctgcgt gcgccggtac ctactctacc accacaacat caacatccct tccaagatca    26760
tccgttacta caaatcctct tcccgttcca gcgatctcca ggaaggccgc agcagcggcg    26820
gcagcagaac cagcccacgt cagccagctg agagctaaga tcttccccac gctgtacgcc    26880
atcttccagc agagccgcgg cggccaggac gccctcaaaa tcaggaaccg caccctgcgc    26940
tccctcacca agagctgtct gtatcaccgc gaggaggcca agctggaacg cacgctctcg    27000
gacgcagaag ctctcttcga gaagtactgc gctcggcagc ggcagacccg ccggtattta    27060
aggagcggac cctgcgtgcg gacacaccat gagcaaacaa atccccaccc cgtacatgtg    27120
gtcttatcag ccacaatctg ggcgtgccgc cggtgcctcc gtcgattact ccacccgcat    27180
gaattggctc agtgccgggc cttccatgat tggccaggtc aatgacatcc gacacaccag    27240
gaaccagatt ctcattcgcc aggcccttat caccgagacg ccacgccccg tccaaaatcc    27300
cccgtcctgg cccgccagcc tgttgcctca gatgacgcaa ccgcccaccc acctgcacct    27360
gccgcgtaac gaaattttgg aaggcagact gactgacgcc ggcatgcaat tagccggggg    27420
cggagccctc gcacccagag acttatatgc cctgacccte cgcggcagag gcatccagct    27480
```

```
caacgaggac ctacccctct cggcgagcac tctccggccg gacggcatct tccagctcgg    27540
aggcggaggc cgctcctcct tcaaccccac cgacgcctac ctgacgctgc agaactccag    27600
ctcccttccc cgcagcggcg gcatcggcag cgagcaattt gtccgcgagt tcgtgcccac    27660
ggtctacatc aaccccttct ccggaccgcc cgggacctac cccgaccagt tcatcgccaa    27720
ctacaacatc ctaacggact ctgtagcagg ctatgactga cggtccccag ggtcagcagc    27780
ggctgcggga gctcctcgac cagcaccgcc gccagtgccc taaccgctgc tgcttcgcca    27840
gggaagggat tcacccggag tacttttgca tcacccgcga gcactttgag gccgagtgca    27900
tccccgactc tctgcaagaa ggccacggtc tgcgcttcag cctccccacg cgctacagcg    27960
accgccgcca ccgcgatgga gaccgcacca tcctcacttc gtactactgc ggccctgctt    28020 cttcaaagt tcgctgtctc tgcggccatc ctgctcctca ccctcttctt ctcgaccttc    28080
tgtgtgagct gtacaaccgc tcgtagcgtc agcccctaca cctcccctcg cgtccaattt    28140
ctgtccgaca tagaaccaga ctctgactct tactcgggct ctggctctgg ggacgatgaa    28200
gattatgaat atgagctggc taccaacaca ccgaacgaag acattctagg cagcatagtc    28260
atcaacaacc agatcgggcc caagaccctg gccctgggat acttttatgc cgccatgcag    28320
tttgtcttct ttgccatcat catcatcgtc ctcatcctct actaccgccg ctacgtgctg    28380
gccaccgccc tcatcgtgca gcgccagatg tggtcctccg aggccgtcct gcggaaaacc    28440
ttctcggcca ccgttgtggt tactccccca aaacaagtca ccccctgcaa ctgctcctgc    28500
cgcttcgagg agatggtgtt ctactacacc acctccgtct tcatgccctg gtgggcctca    28560
tcctcctgct caccgccatg gtccgcctgg ccaactggat agtggatcag atgcccagca    28620
ggaaccgcgc cccgccgctg ccaccgcccc tcacctatgt gggaccctgc gccgaggacc    28680
acatctacga tgagccaacc gtagggcaat acgtacagat gaagtagctc cccctctttc    28740 ccattcccc atttttctct attcaataaa gttgcttacc tgagttcatc cacactcggt    28800
ctgccagtgc agtctatcca tgcgccgttt tccatactca catagcgcag ccgcgcacgc    28860
ctcgccaggt gacgaaactg tcgaaatgta acatttcgcg cttctgtcag cagcaccccg    28920
ttatagacca gttccaccat gggaccgaag aagcagaagc gcgagctacc cgaggacttc    28980
gatccagtct acccctatga cgtcccgcag ctgcagatca atccacccct cgtcagcggg    29040
gacggattca accaatccgt ggacggggtg ctgtccctgc acatcgcacc gccctcgtt    29100 tttgacaaca ccagggccct caccctggcc ttcgggggag gtctacagct ctcgggcaag    29160
cagctcgtcg ttgccaccga gggctcgggg ctaaccacca acccggatgg caagctggtt    29220
ctcaaagtca agtcccccat caccctgacc gccgagggca tctccctgtc cctgggtccc    29280
ggtctttcta actcagagac cggcctcagt ctgcaagtca cagctcccct gcagttccag    29340
ggcaacgccc tcactcttcc cctcgccgcc ggtctccaaa acaccgatgg tggaatgggt    29400
gtcaaactgg ggagcggtct caccacggac aacagtcagg cggtgaccgt tcaggtggga    29460
aatggacttc agctgaacgg cgaaggacaa ctcaccgtcc ccgccacggc cctttagtc    29520 tcagggagcg caggcatctc tttcaactac tccagcaatg acttcgtctt agacaatgac    29580
agtctcagtt tgaggccaaa ggccatctct gtcacccctc cgctgcagtc cacagaggac    29640
acaatctccc tgaattattc taacgacttt tctgtggaca atggcgccct caccttggct    29700
ccaactttca aaccctacac gctgtggact ggcgcctcac ccacagcaaa tgtcattcta    29760
acaaacacca ccactcccaa cggcaccttt ttcctatgcc tgacacgtgt gggtgggtta    29820
gttttgggtt cctttgccct gaaatcatcc atcgacctta ctagtatgac caaaaaggtc    29880
```

```
aattttatttt ttgatggggc aggtcggctt cagtcagact ccacttataa agggagattt    29940
ggatttagat ccaacgacag cgtaattgaa cccacagccg caggactcag tccagcctgg    30000
ttaatgccaa gcacctttat ttatccacgc aacacctccg gttcttccct aacatcattt    30060
gtatacatta atcagacata tgtgcatgtg gacatcaagg taaacacact ctctacaaac    30120
ggatatagcc tagaatttaa ctttcaaaac atgagcttct ccgccccctt ctccacctcc    30180
tacgggacct tctgctacgt gccccgaagg acaactcacc gtccccgcca cggccccttt    30240
agtctcaggg agcgcaggca tctctttcaa ctactccagc aatgacttcg tcttagacaa    30300
tgacagtctc agtttgaggc caaaggccat ctctgtcacc cctccgctgc agtccacaga    30360
ggacacaatc tccctgaatt attctaacga cttttctgtg gacaatggcg ccctcacctt    30420
ggctccaact ttcaaaccct acacgctgtg gactggcgcc tcacccacag caaatgtcat    30480
tctaacaaac accaccactc ccaacggcac cttttttccta tgcctgacac gtgtgggtgg    30540
gttagttttg ggttcctttg ccctgaaatc atccatcgac cttactagta tgaccaaaaa    30600
ggtcaatttt attttgatg gggcaggtcg gcttcagtca gactccactt ataaagggag    30660
atttggattt agatccaacg acagcgtaat tgaacccaca gccgcaggac tcagtccagc    30720
ctggttaatg ccaagcacct ttatttatcc acgcaacacc tccggttctt ccctaacatc    30780
atttgtatac attaatcaga catatgtgca tgtggacatc aaggtaaaca cactctctac    30840
aaacggatat agcctagaat ttaactttca aaacatgagc ttctccgccc ccttctccac    30900
ctcctacggg accttctgct acgtgcccca gagtgcctag agaaccctgg ccgtcagccg    30960
gcctccccct tcccaggcca cccggtacac cacccgctcc atgtttctgt atgtgttctc    31020
ctcccgccgc ttgtgcagca ccacctcccg ctgctcgagc tgaggatccg tgatggacac    31080
aaagccagga agacacatcc tcagctccgt gggggcgtcc aacaactgtt tatgtaaagg    31140
aaaataaaga ctcagagaaa atccaagttc atatgatttt tcttttattg attggggaa    31200 ttgattcagg tggggtgtgc ataatcacaa aaatcacatc agcaggtaca cacctgagac    31260
atcagacagg ggtaaggaca gcgcctcagc ttctggaaca gacatcagaa atatttaatc    31320
tgctggtagc taacactcct tcccaacacc atacactcct ggagggccct ctgcctctcc    31380
tcctcccgct ccgcgtccct ctgccgggac caccactccc cctccgtgaa ctgctgcttc    31440
ctcccccgcc gctgcgcccc gatggcctcc gccgccagct tcagccagtg ccgcaagcgc    31500
tgggcgcagc gccgagccac cggctcgctc agctcgtggc agcgccggca caccagcact    31560
atgtaattgg catagtcccc gtcacagtag atgacctccc cccagtggaa catgcgcaac    31620
agcttcagat cacagtcata catgatcttt atgtacatca ggtgggcgcc tcgaaacatc    31680
acactgccca cgtacatcac gcgactcacg ctgggcaggt tcaccgcctc cctgaaccac    31740
cagaagatgc gattgtactc gcagccccgg atgatctcgc gcatcaggga gcgcatcacc    31800
acctgccccg cgcggcactc cagactggac cttttcgac agtggcaatg aaagttccac    31860
agcgtcgcgc ccgcacagcg tctccgggct gaaacatatc tgctccagct ccaacccccc    31920
acacaggctg tactgcagga aaatccattc ttgatgggaa aggatgtagc gccagggac    31980 cacaatctcc aaacagggaa caaaacatac cgcggcccgg ctgttgcgca cggcccccac    32040
cggatgcaac gtgctcacgg agcagatacg ggtgggacag cggcccacgt ctcatagcaa    32100
gtcaagtccg gaagtggcac ggggttcgcc accactgcta ctgctgccgc tgcgccacca    32160
gctccatcgg ctcctccatc ctcctcctgt tccatcggct gaggtgctgc ctcctcctcc    32220
tcctgccgct gctccatcat gctcgtctgc ggtcatcagg agtcaaaaaa ttcattggcc    32280
```

-continued

```
accgcacgca gagagaacat ggagcgcagg ggcccaggtg cccggcccgt gcgctcgctc   32340
aactccccca gcaggtactc atagagatgc tcctccaaat ccaccgcaaa ccaggcatgc   32400
agaaactctt ccgttcgagg accgcccacg gtaaagacat agccctcccg caccttcacc   32460
gctgccagct gcacgcgctc atgtcgctgg gagtacaccc ggacccgggc ctggatgtac   32520
tccagcacct gatcgctcag acacctcaca gagatgccag cctgagccag cttctcatag   32580
agaggtggct gaatcttgag cttgaagcag cgagcggcta ggcactcccc gccccttgg    32640
aacagggcgg ccgggtcagc catggacttc ctctacatcc ggggtcctgg ccacctcaca   32700
aactatctgg ccaatcgcct gaccacgggt caccaggtaa ggatgatgtc cgttgttgcg   32760
aatgagaatg ctcagaggtg actcggtagc gttatcaatc acgtcccaa aggtccaaag    32820
gtcccagtta gaagtcaggt gcttcagacc gcagacacgc ccatagcaac cagtgggaaa   32880
agccagcaag agatccgtgg gcacatgcac cgaagctccc gcaggaatct ccacccactc   32940
cgaggcgtag accgtgtaag ctacacaccc cgcctcccga gtgggagcag aagcattctc   33000
gctcagccga aagaacttca gggtggcctg catatcctct tttactcact tgttagcagc   33060
tccacacaga ccagggttgt gttggcggga ataggcagca ggggtacgtc cccagtgagg   33120
gacacctgga tggggggcag aggattgatg ccaggaagca gcaggtactg ggaaacagag   33180
accagatccc tcctctgaaa aatctcgctc agtcggacaa acacagcaaa cccagtgggc   33240
acgtagacta gcacattaaa aaggatcacg ctgggctgtt ctgacgtcag caccagatgt   33300
cgggacgtgc gcagatgaat gcggttctga tgaattaccg gaggcctctc acccgcagcc   33360
aacagcagac cgggctgctg atgcggtccc gcagacatat atgagttcaa tgtgtgtctt   33420
ttttctaaac gtctagtgag tgtgctcgtc ctgctcctgc caatcaaaat ccgggcacca   33480
gggctggtgg ttggacccga tgaagaagcg aggagaggcg gcctcctgag tgtgaagagt   33540
gtcccgatcc tgccacgcga ggtaggcgaa gtacagatag agcacggcga gaacagtcag   33600
caccgcggcc agcagcagtc ggtcgtgggc catgagaggg ggctgatggg aagatggccg   33660
gtgactcctc tcgccccgct ttcggttct cctcgtctcg ctctcagtgt ctctctctgt    33720
gtcagcgccg agacgagtgt gagcgaacac cgcgagcggg ccggtgatat acccacagcg   33780
gatgtggcca cgcctgcggt cggttaatca gtaccccatc gtccgatcgg aattcccccg   33840
cctccgcgtt aacgattaac ccgcccagaa gtcccgggaa ttcccgccag ccggctccgc   33900
cgcgacctgc gactttgacc ccgcccctcg gactttgacc gttcccacgc cacgtcattt   33960
tcccacgcga cgtcacgttc ccacgctacg tcacacccct ctccaccaat caccgcccgc   34020
cgcccccaac cctctccgcc aatcaccacg ccacaaaagg ggcaataaaa gtgtgcggta   34080
tattattgat gatg                                                    34094
```

VIRAL VECTORS AND VIRAL VACCINES BASED ON RECOMBINANT PORCINE ADENOVIRUSES

The present invention relates to serotype 3 and serotype 5 porcine adenoviruses which are recombined by insertion of heterologous nucleotide sequences, these adenoviruses being capable of replicating autonomously in vivo and of expressing these heterologous sequences. The invention also relates to the porcine vaccines obtained, to methods for immunizing pigs using them, to deleted and replicative adenoviral vectors, and to methods for obtaining these adenoviruses, vaccines and vectors.

The documents cited in the description and also the documents cited in those documents are incorporated herein by way of reference.

Adenoviruses are viruses containing a linear double-stranded DNA molecule, with inverted terminal repeat sequences at each end. Adenoviruses are part of the family of Adenoviridae, which are responsible for diseases affecting a large number of species, such as the simian, bovine, ovine, porcine, equine, murine, canine and avian species. Adenovirus infections can be characterized, depending on the species and on the types of adenovirus, by signs of encephalitis, of pneumonia, of renal lesions, of diarrhea and of hepatitis.

The adenovirus genome can vary from one species to the other [(T. Adrian et al., Arch. Virol. 1986, 91, 277–290), (J. Hamelin et al., J. Clin. Microbiol. 1988, 26, 31–33), (R. Assaf et al., Can. J. Comp. Med. 1983, 47, 460–463), (T. Kurokawa et al., J. Virol. 1978, 28, 212–218), (S.-L. Hu et al., J. Virol, 1984, 51, 880–883), (L. Zsak et al., Intervirology 1984, 22, 110–114)]. Animal adenoviruses, unlike human adenoviruses, have a very limited host spectrum and they often infect only the animals belonging to their species of origin.

The first porcine adenovirus (or PAV) was isolated in 1964 (D. Haig et al., J. Comp. Pathol. 1964, 74, 81–84). Since that date, 5 porcine adenovirus serotypes have been identified and described (Hirahara et al., J. Vet. Sci. 1990, 52, 407–409). Serotype 1 and serotype 2 adenoviruses are associated with diarrhea; serotype 4 adenoviruses are associated with symptoms of pneumonia and of encephalitis. Porcine adenoviruses have been classified in a fifth serotype due to their absence of cross-neutralization with antiserum specific for the serotype 1 to serotype 4 PAVs. The genome of PAV-5 has been analyzed and a restriction map has been established (Tuboly et al., Virus Res. 1995, 37, 49–54). This analysis showed the absence of similarity between the PAV-5 restriction maps and those of the PAVs of the other serotypes: PAV-1 and PAV-2 (Reddy et al., Arch. Virol. 1995, 140, 195–200, PAV-3 (Reddy et al., Intervirology 1993, 36, 161–168) and PAV-4 (Kleiboeker et al., Arch. Virol. 1993, 133, 357–368) Among the serotypes 3 and 5, strains exist which are naturally nonpathogenic for pigs.

PAVs have a genome which is approximately 32 to approximately 34 kbp in size. The genome of PAV-1 is approximately PAV-2 is approximately 33.3 kbp in size. The complete sequence of the PAV-3 virus has recently been established and filed in the GenBank data bank under the number AF083132 (SEQ ID NO: 6) (P. S. Reddy et al., Virol. 1998, 251, 414–426); it is 34094 base pairs (bp) in size. The genome of PAV-4 is approximately 32 kbp in size and that of PAV-5 is approximately 33.2 kbp in size. The complete genome of PAV-5, and in particular the E3 region, has not been sequenced or published.

The main application envisaged for adenoviruses is in the field of gene therapy in humans, and a very large number of constructs and systems have been proposed. Adenoviruses have also been proposed as recombinant vectors in immunization compositions for protecting humans and animals against many pathogenic viruses.

To date, two strategies for constructing recombinant adenoviral vectors have been developed (M. Eloit & M. Adam, J. Gen. Virol. 1995, 76, 1583–1589).

The first strategy consists of the insertion of expression cassettes into regions which are essential for replication of the adenovirus, hence the need to develop transcomplementation systems, in parallel, in order to be able to ensure the replication of the virus. For porcine adenoviruses, the E1 region has been proposed as an insertion site (P. S. Reddy et al., Virus Res. 1998, 58, 97–106). The recombinant vectors thus constructed are termed "nonreplicative" since they cannot replicate in the host to which they are administered.

As a variant of this first strategy, it is possible to use a virus which is nonreplicative in the target animal. The PRV gD expression cassette has in particular already been inserted into the E1A site of the serotype 5 human adenovirus, which is nonreplicative in pigs (M. Monteil et al., J. Gen. Virol. 1997, 78, 3303–3310; A. Ambriovic et al., Virol. 1997, 238, 327–335).

The second strategy consists of the insertion of expression cassettes into regions of the viral genome which are not essential for replication of the adenovirus. The difficulty in determining nonessential regions in adenoviruses and the presence of a rigid capsid make this second strategy difficult to carry out.

Specifically, one of the essential characteristics of adenoviruses is that they have a rigid capsid which strictly limits the size of the DNA molecule which may be encapsidated therein. In general, it is considered possible to encapsidate a DNA molecule corresponding to 105 to 114% of the size of the genome, which corresponds, depending on the size of the genome, to inserts of approximately 1.7 to approximately 3.9 kbp. In the case of excessive sizes, unwanted deletions and/or rearrangements in the recombinant genome may take place.

The E3 region is neither conserved in terms of size nor in terms of genetic organization from an adenovirus of one given species to an adenovirus of another species, nor between porcine adenoviruses of the various serotypes (S. Kleiboeker, Virus Res. 1994, 31, 17–25).

The E3 region of the PAV-3 virus is 1179 base pairs in size. It is a complex region which encodes at least three open reading frames (ORFs). These ORFs overlap one another, and the first ORF also partly overlaps the gene encoding the pVIII protein (P. S. Reddy et al., Virus Res. 1995, 36, 97–106), which is an essential protein.

The presence of these overlapping ORFs in the E3 region represents a major difficulty for determining therein the insertion sites and/or the deletion limits such that the recombinant adenoviruses remain replicative in pigs.

The amino acid sequence encoded by the second ORF of the E3 region shows no homology between the PAV-3 adenovirus and the HAV-2 adenovirus (which is a serotype 2 human adenovirus), nor with any other currently known adenoviral protein (P. S. Reddy et al., Virus Res. 1995, 36, 97–106). The amino acid sequences predicted from the nucleotide sequence of the first ORF of the E3 region in PAV-3 have only 33.3% identity with that of the serotype 2 canine adenovirus (CAV-2). Not only are the proteins encoded by E3 regions from various adenoviruses not homologous, but, in addition, those encoded by the ORFs of the E3 region show no homology between the PAV-3 and PAV-4 adenoviruses (S. B. Kleiboeker, Virus Res. 1994, 31, 17–25).

The E3 region is 1162 bp in size in PAV-1 (with 5 ORFs); it is 1222 bp in PAV-2 (with 5 ORFs) (P. S. Reddy et al., Virus Res. 1996, 43, 99–109), and 1879 bp in PAV-4 (with 6 ORFs). Only the fourth ORF of the E3 region of the PAV-4 virus (corresponding to a 13.2 kDa protein) shows homology with another known ORF of the E3 region, encoding the 14.7 kDa protein of the type 5 human adenovirus (known as Human Adenovirus 5 or HAV-5). The E3 region of PAV-4 shows no sequence homology with the E3 regions of the other porcine adenoviruses, and in particular with those of PAV-3 and of PAV-5.

Besides the difficulty in defining their limits for conserving the replicative nature in vivo, deletions in the E3 region are, moreover, not without risk. Deletions in the E3 region may, in fact, have consequences on the pathogenicity of the recombinant adenoviruses. Thus, it has been observed that a deletion in the E3 region of the HAV-5 virus increases the pulmonary pathogenicity of this virus in the cotton rat experimental model of infection (Ginsberg et al., Proc. Natl. Acad. Sci. USA 1989, 86, 3823–3827).

This shows that the consequences of deletions in the E3 region of an adenovirus must be considered case by case and not by simply transposing the observations made on one particular adenovirus to another. The genetic organization of the E3 region of PAV-3 is unique, as is that of the E3 region of PAV-5.

The precise location of an insertion site in the E3 region is further complicated by the fact that complex splicing zones and polyadenylation zones are present, these zones being characteristic of adenoviruses (Imperiale et al., Curr. Top. Microbial. Immunol. 1995, 199, 139–171). The splicing zones located in the E3 region are important for the maturation of many essential messenger RNAs encoded by the sequences located outside the E3 region. The E3 region is, itself, located in a part of the viral genome which displays high transcriptional activity (P. Sharp, 1984, in The Adenovirus, Ed. H. S. Ginsberg, Plenun Press, New York and London, 173–204); the insertion of a heterologous nucleotide sequence into the E3 region may have negative impacts on the biological activity of the recombinant virus. In addition, the E3 region is located downstream of the major late promoter (MLP), this being a region in which interference between the transcription of the insert and that initiated by the MLP promoter have been demonstrated (Xu et al., J. Gen. Virol. 1995, 76, 1971–1980).

The results obtained with adenoviruses originating from other species (human, bovine, ovine, etc.) cannot therefore be transposed to porcine adenoviruses. No replicative recombinant vector has thus been produced to date from a porcine adenovirus.

The Applicant Company set itself the aim of making possible the insertion of heterologous genes into the genome of the PAV-3 and PAV-5 viruses without substantially modifying their capacity for replication in vivo.

Another aim of the invention is to provide insertion regions which can be deleted without placing this capacity for replication in doubt, so as to increase the capacity for insertion into the virus.

Yet another aim of the invention is to provide recombinant PAV-3 and PAV-5 viruses which conserve a capacity for replication in vivo, allowing their use as live recombinant vaccines, including vaccines administered mucosally and/or in the presence of antibodies of maternal origin.

The Applicant Company has succeeded in modifying the E3 region of PAV-3 and PAV-5 while at the same time conserving the capacity for replication in vivo. It has also been able to demonstrate the in vivo expression of a gene inserted into this region. It therefore makes it possible for PAV-3 and PAV-5 to be used as replicative expression vectors.

A subject of the present invention is therefore a serotype 3 or 5 porcine adenovirus comprising at least one heterologous nucleotide sequence inserted into the genome of PAV-3 or of PAV-5, under conditions which allow the recombinant viruses obtained to replicate in vivo in pigs and to express the inserted sequence. These modified viruses have considerable advantages in terms of vaccination and, in particular, they are effective even in the presence of maternal antibodies and can then be effectively used mucosally.

Preferably, a heterologous sequence is inserted into a nonessential zone of the genome, in particular the E3 zone, with a deletion of this insertion zone. The expression "deletion of a zone" is intended to mean a total or partial, preferably total, deletion of the insertion zone. In other words, the heterologous sequence is inserted in place of all or part of the insertion zone, preferably in place of all of this zone.

For PAV-3, the preferred zone for insertion into E3 is a zone comprising all or part of nucleotides 706 to 1624 of the sequence published by P. S. Reddy et al., Virus Research 1995. 36-97-106, which corresponds to positions 27 794 to 28 712 of the sequence published in GenBank AN # U10433. In other words, this insertion zone and its possible deletion can comprise all or only part of the sequence 706 to 1624 and/or can extend in E3 beyond the limit 706 and/or the limit 1624 and can optionally comprise the entire E3. Preferably, this zone consists, or comprises, E3, nucleotides 706 to 1624, nucleotides 1002 to 1624, or all or part of the sequence 706 to 1002. In particular, it comprises at least the sequence 1002 to 1624.

For PAV-5, E3 is defined by the nucleotide sequence 2382 to 4042 in SEQ ID No. 5. The insertion zone and its possible deletion includes E3 and comprises all or part of nucleotides 2064 to 4083, for example all or part of nucleotides 2389 to 3861, of SEQ ID No. 5 (FIG. 13). In other words, this insertion zone and its possible deletion can comprise only part of the sequence 2389 to 3861 and/or can extend in E3 beyond the limit 2389 and/or beyond the limit 3861 and can optionally comprise the entire E3. When a deletion is made up to nucleotide 4083 inclusive, a splice acceptor site is then preferably inserted in place of nucleotide 4083. Preferably, this insertion zone consists essentially of nucleotides 2389 to 3861.

Needless to say, the invention also covers the insertion into the corresponding zones defined by the nucleotide sequence of other strains of PAV-3 and of PAV-5, the sequences of which differ from those of the reference strains according to the invention.

A subject of the invention is also a PAV-3 or PAV-5 virus which has a greater capacity for insertion in terms of size, while at the same time remaining replicative in vivo in pigs. Maintaining the property of replication in the host is desired in order to obtain optimum protection effectiveness, in particular using an immunization composition mucosally and/or in the presence of antibodies of maternal origin.

Increasing the capacity for insertion is achieved by means of a deletion, e.g. of all or part of the E3 region, the part of E3 which can be deleted being located between the gene encoding the pVIII protein and that encoding the fiber. In particular, the present invention describes deletions of 622 bp and 919 bp which can be made in the E3 region of the PAV-3 virus, while at the same time conserving the replicative nature of the recombinant viruses (see examples 6 to 10). The present invention moreover describes a deletion of 1472 bp in the E3 region of the PAV-5 virus, resulting in the same phenotypic characteristics of the recombinant virus (see examples 14 to 17).

The recombinant PAV-3 or PAV-5 adenovirus obtained according to the invention may advantageously be used to insert a maximum size of approximately 3.0 kbp for the PAV-3 virus and approximately 3.5 kbp for the PAV-5 virus and to express it in pigs.

A subject of the invention is thus also the PAV-3 and PAV-5 vectors deleted, in particular in the E3 region, while at the same time remaining replicative, in particular deleted in the abovementioned zones, i.e. deleted of all or part of the zone considered, preferably of all of this zone.

The heterologous nucleotide sequences which may be inserted are sequences encoding immunogens or immunologically active fragments, e.g. epitopes, of immunogens, and in particular genes or fragments of genes (e.g. epitopes) encoding immunogens of porcine pathogens.

In the context of the present invention, it is of course possible to insert more than one heterologous sequence into the same virus. In particular, heterologous sequences originating from the same virus or from different viruses may be inserted therein.

According to one particular method, it is possible to insert artificial sequences combining several fragments or epitopes originating from the same pathogen or from different pathogens, which are known as "polyepitope sequences". In the latter case, the polyepitope sequence is placed under the control of a single promoter.

It is also possible to insert sequences encoding immunomodulators, in particular cytokins, preferably porcine cytokins such as porcine granulocyte-macrophage colony stimulating factor (poGM-CSF) porcine interleukin 4 (poIL-4), porcine IL-12 or porcine IL-18.

The expression of several heterologous genes inserted into the insertion locus can also be made possible by inserting a sequence known as an "IRES" (Internal Ribosome Entry Site) in particular originating from a picornavirus such as swine vesicular disease virus (SVDV; B.-F. Chen et al., J. Virology, 1993, 67, 2142–2148), encephalomyocarditis virus (EMCV; R. J. Kaufman et al., Nucleic Acids Research, 1991, 19, 4485–4490) or foot-and-mouth disease virus (FMDV; N. Luz and E. Beck, J. Virology, 1991, 65, 6486–6494), or from another origin. Those skilled in the art may refer to the content of the 3 articles cited. The expression cassette for two genes would therefore have the following minimum structure: promoter (optional)-gene 1-IRES-gene 2-polyadenylation signal. The live recombinant vaccine according to the invention may therefore comprise, inserted into the insertion locus, an expression cassette successively comprising a promoter, two or more genes separated in pairs by an IRES, and a polyadenylation signal.

The porcine pathogens are viruses, bacteria and parasites chosen in particular from those of the group consisting of Aujeszky's disease virus (PRV or pseudorabies virus), swine influenza virus (SIV), porcine reproductive and respiratory syndrome virus (PRRS virus), parvovirosis virus (PPV virus), Hog Cholera Virus (HCV), porcine circovirus, in particular type 2 porcine circovirus (Porcine CircoVirus type 2, PCV2 or piglet systemic wasting syndrome virus), *Actinobaccilus pleuropneumoniae* and *Mycoplasma hyopneumoniae.*

With regard to the Aujeszky valency, it is possible to use the gB gene (Robbins A. K. et al., J. Virol. 1987, 61, 2691–2701 GenBank AN # M17321), gC gene (Ishikawa K. et al., Vet. Microbiol. 1996, 49, 267–272 GenBank AN # D49435) and/or the gD gene (Rivière M. et al., J. Virol. 1992, 66, 3424–3434 and Hong W. Z. et al., GenBank AN # AF086702), in their native or secreted forms.

With regard to the swine influenza valency, it is preferred to use the HA gene (WO-A-98/03658, examples 10 and 12) (native or secreted forms), the NA gene (Nerome K. et al., J. Gen. Virol. 1995, 76, 613–624 GenBank AN # D21194) (native or secreted forms) and/or the NP gene (WO-A-98/03658, examples 11 and 13).

With regard to the PRRS valency, it is preferred to use the ORF4 gene, the ORF3 gene (native or secreted forms), the ORF5 gene (native or secreted forms), the ORF6 gene and/or the ORF7 gene from European strains (Meulenberg J. et al., Virology, 1993, 192, 62–72) and from American strains (Mardassi H. et al., Arch. Virol. 1995, 140, 1405–1418).

With regard to the hog cholera valency, it is preferred to use the EO gene, the E1 gene (native or secreted forms) and/or the E2 gene (native or secreted form) (Meyers G. et al., Virology, 1989, 171, 18–27).

With regard to the parvovirosis valency, it is preferred to use the VP2 capsid gene (Vasudevacharya J. et al., Virology, 1990, 178, 611–616).

With regard to the PCV2 valency, it is preferred to use the ORF1 and/or ORF2 genes, but preferably ORF1 and ORF2 (Meehan B. et al., J. Gen. Virol. 1998, 79, 2171–2179).

The heterologous sequences are inserted under the control of regulatory signals for transcription and in particular of a promoter, preferably introduced during the recombination. However, it is not excluded to express these heterologous sequences under the control of signals intrinsic to the adenovirus acting as the vector.

Among the useful promoters which are preferably used are strong eukaryotic promoters, such as the Rous sarcoma virus LTR and, preferably, the cytomegalovirus immediate-early (CMV-IE) promoter, in particular of murine origin (MCMV-IE) or human origin (HCMV-IE), or alternatively those of other origins, e.g. from pig, monkey, rat or guinea pig.

In a particularly advantageous manner, the CMV-IE promoters can be used with an enhancer (U.S. Pat. No. 5,168,062, U.S. Pat. No. 4,968,615, U.S. Pat. No. 4,963,481). It may be advantageous to use the fragments of these promoters, which conserve the promoter activity, preferably with the enhancer, e.g. the truncated CMV-IE promoters according to WO-A-98/00166. For further details, those skilled in the art may refer to WO-A-98/00166, and in particular example 12 therein.

The subject of the present invention is also the immunogenic or immunological preparations, and the porcine vaccines, comprising a recombinant adenovirus in accordance with the invention, in a vehicle or an excipient which is acceptable from a veterinary point of view, and optionally an adjuvant. By definition, an immunogenic or immunological preparation induces at least an immune response (cellular and/or humoral) after it has been administered to an animal. A vaccine induces a protective response.

The adjuvants are preferably chosen from acrylic or methacrylic acid polymers and copolymers of maleic anhydride and of an alkenyl derivative.

The preferred compounds are acrylic or methacrylic acid polymers which are crosslinked, in particular with polyalkenyl ethers of sugars or of polyalcohols. These compounds are known by the term "carbomer" (Pharmeuropa Vol. 8, No. 2, June 1996). Those skilled in the art may also refer to U.S. Pat. No. 2,909,462 which describes such acrylic polymers crosslinked with a polyhydroxy compound containing at least 3 hydroxyl groups, preferably not more than 8, the hydrogen atoms of at least three hydroxyls being replaced with unsaturated aliphatic radicals containing at least 2 carbon atoms. The preferred radicals are those containing from 2 to 4 carbon atoms, e.g. vinyls, allyls and other ethylenically unsaturated groups. The unsaturated radicals can, themselves, contain other substituents, such as methyl. The products sold under the name Carbopol® (BF Goodrich, Ohio, USA) are particularly suitable. They are crosslinked with an allyl sucrose or with allylpentaerythritol. Among these, mention may be made of Carbopol® 974P, 934P and 971P.

Among the copolymers of maleic anhydride and of an alkenyl derivative, preference is given to the EMAs® (Monsanto) which are copolymers of maleic anhydride and of ethylene, which may be linear or crosslinked, for example crosslinked with divinyl ether. Reference may be made to J. Fields et al., Nature, 186, 778–780, Jun. 4, 1960.

In terms of their structure, the acrylic or methacrylic acid polymers and the EMAs® are preferably formed from base units of the following formula:

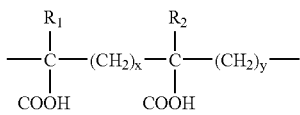

in which:
$R_1$ and $R_2$, which may be identical or different, represent H or $CH_3$
X=0 or 1, preferably x=1
Y=1 or 2, with x+y=2.
For the EMAs®, x=0 and y=2. For the carbomers, x=y=1.

Dissolution of these polymers in water gives an acidic solution which will be neutralized, preferably to physiological pH, to give the adjuvant solution into which the actual vaccine will be incorporated. The carboxylic groups of the polymer are then partly in COO⁻ form.

Preferably, a solution of adjuvant according to the invention, in particular of carbomer, is prepared in distilled water, preferably in the presence of sodium chloride, the solution obtained being at acid pH. This stock solution is diluted by adding it to the amount required (to obtain the final concentration desired), or a large proportion thereof, of water containing NaCl, preferably physiological saline (6 g/l NaCl), in one or more stages with concomitant or subsequent neutralization (pH 7.3 to 7.4), preferably with NaOH.

This solution at physiological pH will be used, without further modification, to take up the vaccine, which is in particular stored in lyophilized form.

The polymer concentration in the final immunization composition will be from 0.01% to 2% W/V, more particularly from 0.06 to 1% W/V, preferably from 0.1 to 0.6% W/V.

The immunogenic preparations and vaccines according to the invention can comprise several recombinant adenoviruses in accordance with the invention, comprising different heterologous nucleotide sequences originating from identical and/or different pathogens.

A subject of the present invention is also the methods for immunizing and for vaccinating pigs against one or more porcine pathogens, comprising the administration of effective doses of the above immunogenic preparations and vaccines. The doses will, for example, be from 1 to $10^7$ $CCID_{50}$.

The invention relates in particular to the administration of these immunogenic preparations and vaccines mucosally, e.g. orally, nasally or ocularly, and/or to young animals exhibiting maternal antibodies. The other routes conventionally used for vaccinating pigs (intramuscular in particular, intradermal, etc.) can also be used.

A subject of the present invention is also methods for obtaining recombinant PAV-3 and PAV-5 vectors, and immunogenic preparations and vaccines incorporating them.

A subject of the invention is also the use of these vectors for the manufacture of the immunogenic preparations and vaccines according to the invention, which are in particular intended for mucosal administration and/or for administration to young animals exhibiting maternal antibodies and/or for administration via the conventional routes.

A subject of the present invention is also a fragment of PAV-5 DNA which includes E3 and which, in the particular strain used here, has the nucleotide sequence referred to as SEQ ID NO. 5. The invention also relates to any fragment of this sequence, in particular any fragment which conserves the PAV-5 specificity. A subject of the invention is thus the sequence 2064 to 4083 and fragments thereof, in particular the E3 sequence of PAV-5 which, in the particular strain used here, is defined by nucleotides 2382 to 4042, and also fragments thereof, in particular all or part of the sequence from 2389 to 3861 in SEQ ID NO. 5. It goes without saying that the invention automatically covers the equivalent sequences, i.e. sequences which do not change the PAV-5 strain functionality or specificity of the sequence described or of the polypeptides encoded by this sequence. Needless to say, sequences which differ through degeneracy of the code will be included.

The invention also covers the sequences specific for PAV-5, which are equivalent in the sense that they are capable of hybridizing to the sequence above under highly stringent conditions and/or in that they have strong homology with the strains of the invention, especially homology greater than or equal to 85%, in particular to 90% and more particularly to 95%.

The invention will now be described in greater detail with the aid of the embodiments given by way of nonlimiting examples, and with reference to the drawing in which:

List of figures:

FIG. 1: Scheme of the pKS-Right ITR3, pPolyII Right ITR3 and pITRsPAV3 plasmids

Figure 2:
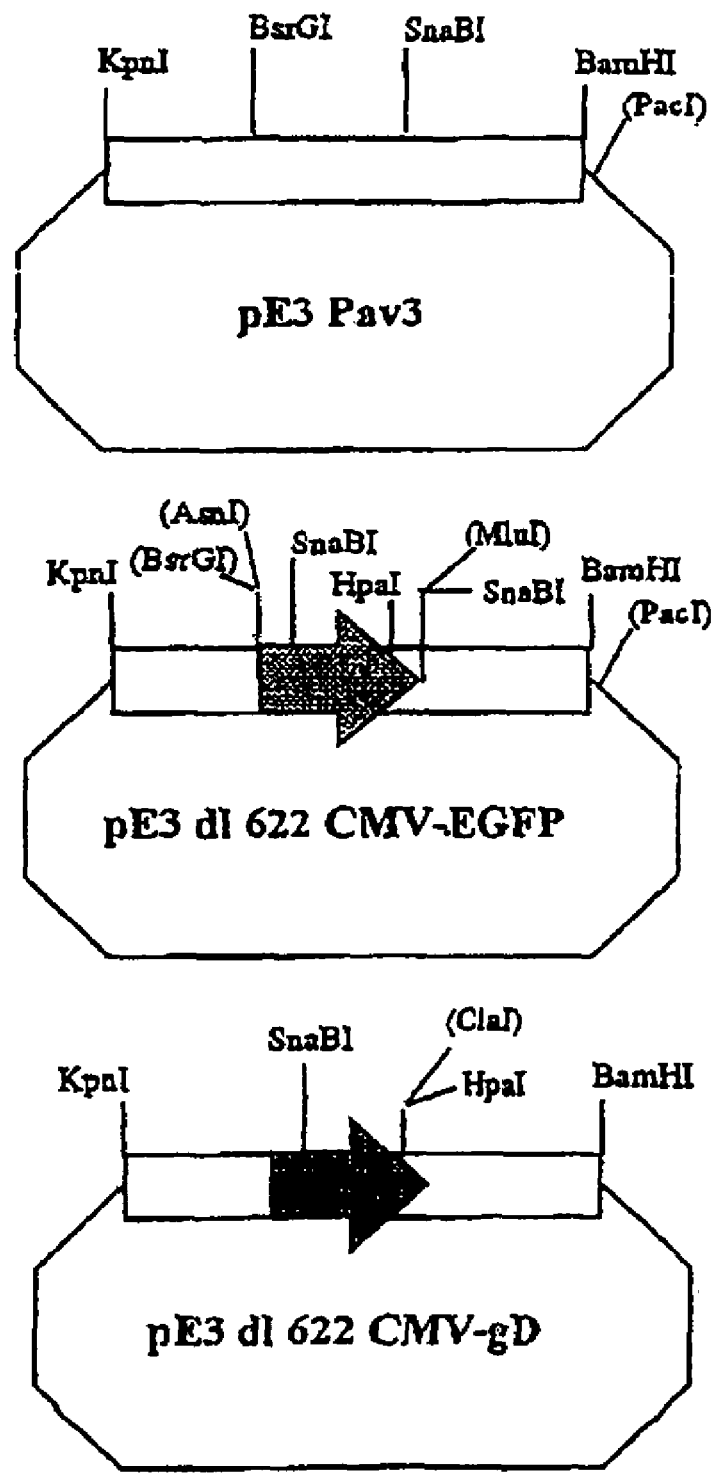

FIG. 2: Scheme of the pE3PAV3, pE3dl622CMV-EGFP and pE3dl622CMV-gD plasmids

Figure 3:
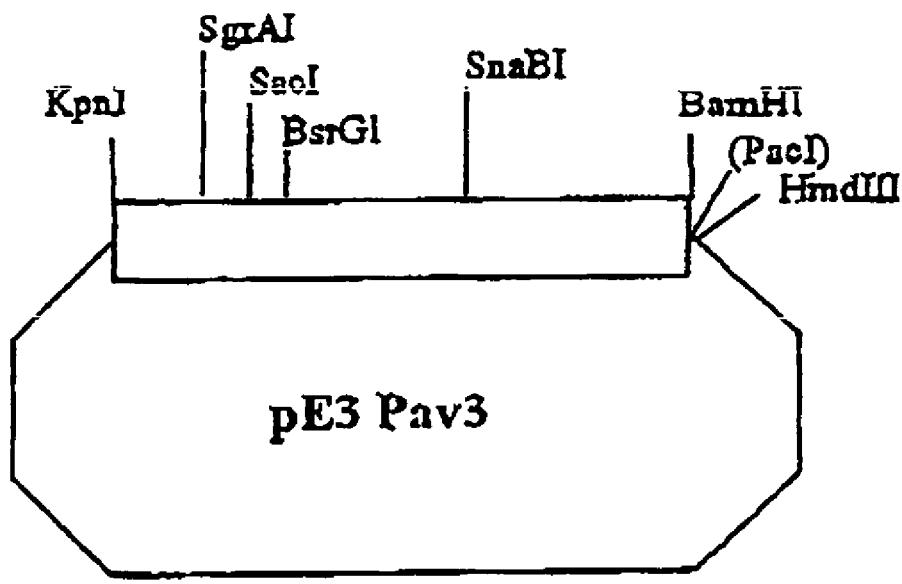
Figure 3:
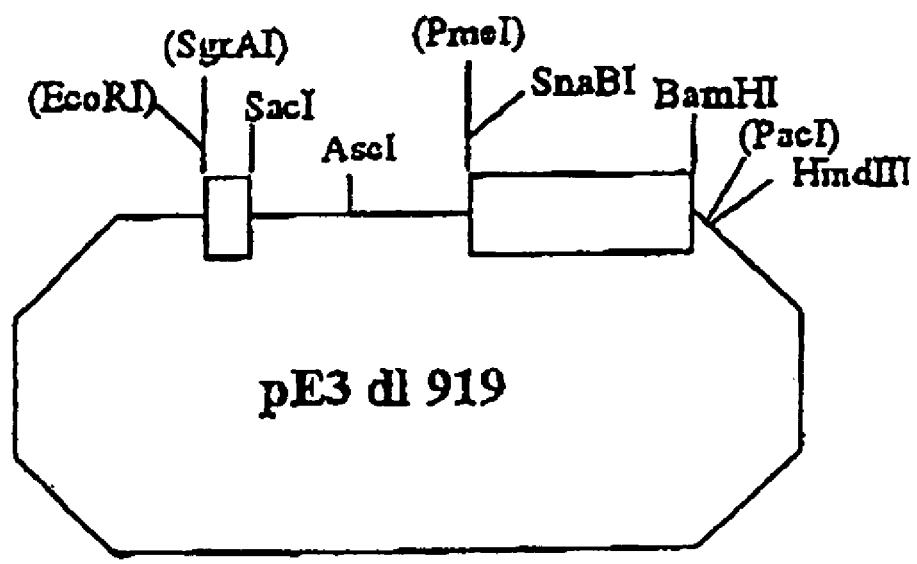

FIG. 3: Restriction map of the pE3PAV3 and pE3dl919 plasmids

Figure 4:
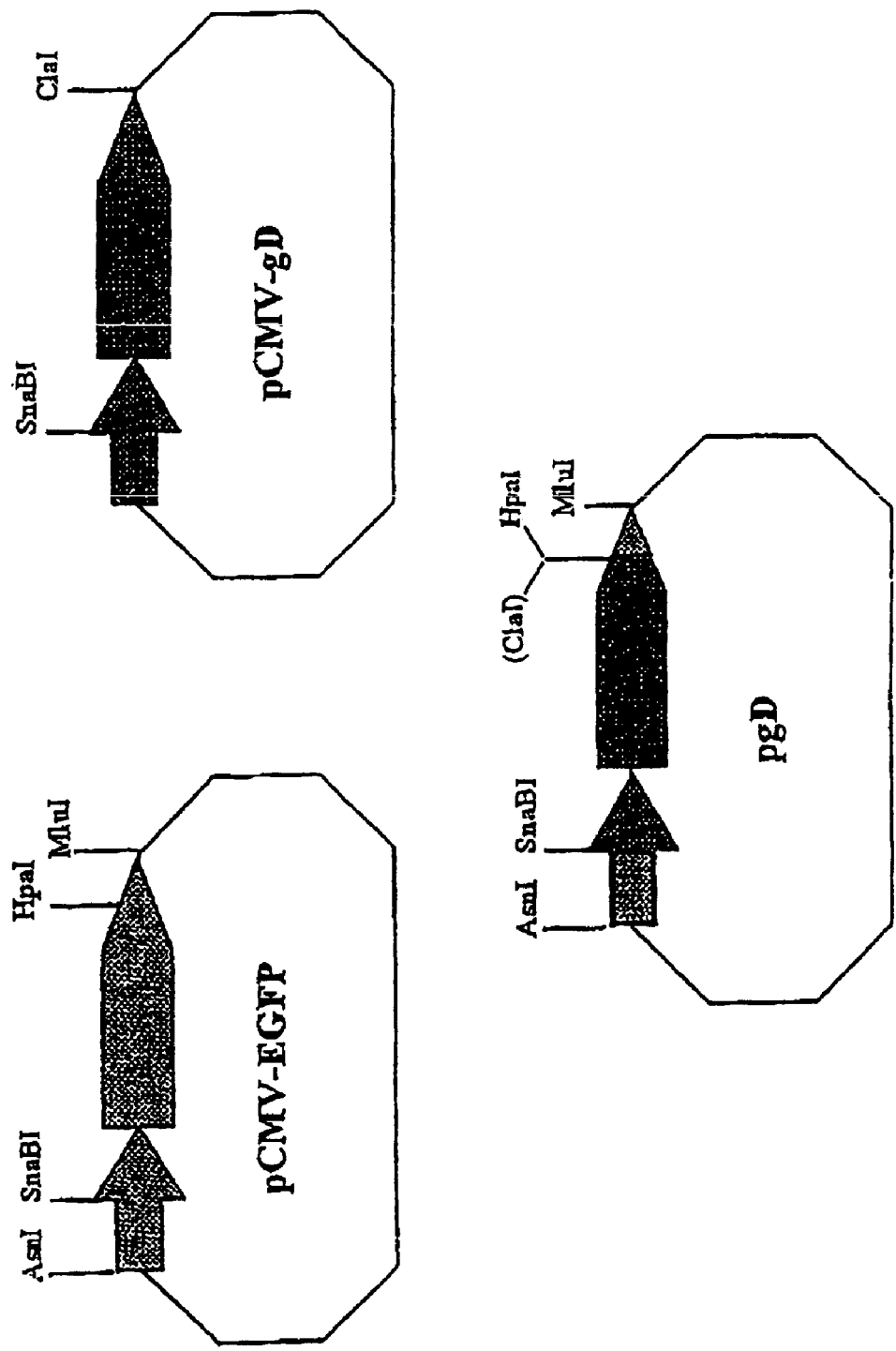

FIG. 4: Scheme of the pCMV-EGFP, pCMV-gD and pgD plasmids

Figure 5:
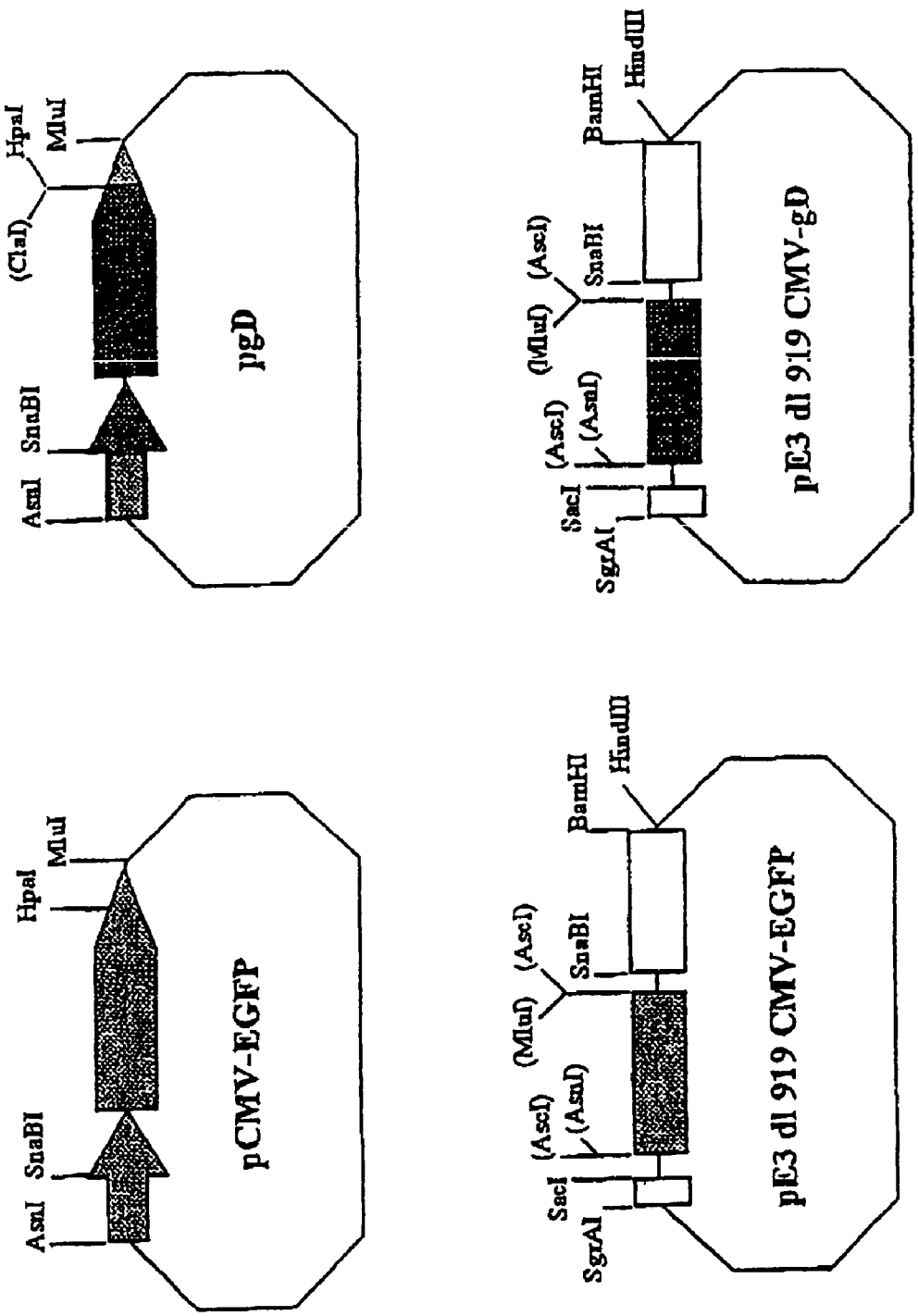

FIG. 5: Restriction map of the pCMV-EGFP, pgD, pE3dl919CMV-EGFP and pE3dl919CMV-gD plasmids FIG. 6: Restriction map of the pE3dl622EGFP and pE3dl919EGFP plasmids FIG. 7: Restriction map of the pE3dl622gD and pE3dl919CMV-gD plasmids FIG. 8: Restriction map of the pCR-Right ITR5, pCR-Left ITR5, pPolyII-Right ITR5 and pITR-PAV5 plasmids FIG. 9: Restriction map of the pE3PAV5 plasmid FIG. 10: Restriction map of the pE3dln472CMV-EGFP and pE3dl1472CMV-gD plasmids FIG. 11: Restriction map of the pE3dl1472EGFP and pE3dl1472gD plasmids FIG. 12: Physical map of PAV-5, digested with BamHI FIG. 13: Sequence of 5614 base pairs (E3 region and adjacent sequences of the PAV-5 virus)

SEQUENCE LISTING

SEQ ID NO 1: Oligonucleotide ITRPAV3
SEQ ID NO 2: Oligonucleotide T3
SEQ ID NO 3: Oligonucleotide T7
SEQ ID NO 4: Oligonucleotide ITRPAV5
SEQ ID NO 5: Sequence of the E3 region of the PAV-5 virus Examples Example 1

Cells and Viruses

The cell culture media and the reagents were supplied by Gibco BRL. The media (Dulbecco's MEM with Glutamax-1 Cat # 61965-026) were supplemented with 1 mM sodium pyruvate (Cat # 11360-039), gentamycin (50 µg/ml, Cat # 15710-031) and 10% fetal calf serum (Cat # 10270-106 batch 40Q5774K).

PK-15 cells (ATCC No. CCL33) and ST cells (ATCC No. CRL 1756) were used for culturing the viruses.

The wild-type type 3 porcine adenovirus (=PAV-3), which is nonpathogenic in pigs, was obtained from the laboratory of Dr. Eva Nagy (University of Guelph, Pathobiology Department, 50 Stone Road Guelph, Ontario, Canada, N1G 2W1) (Reddy P. et al., Virus Res. 1996, 43, 99–109).

The wild-type type 5 porcine adenovirus (=PAV-5), which is nonpathogenic in pigs, was obtained from the laboratory of Dr. Tadashi Hirahara (Kyoto Biken Laboratories Inc., Division of Veterinary Microbiology, 24–16 Makishima-cho, Uji-shi, Kyoto, 611 Japan) (Hirahara T. et al., J. Vet. Sci. 1990, 52, 407–409). Culture and passage conditions: twice a week, the cells are trypsinized (2.5% trypsin solution (Sigma Cat # 044-5075) diluted 50-fold in Earle's balanced salt solution (Gibco-BRL Cat. # 14155-030)) and resuspended in culture medium (dilution 1:6). The cells are cultured at +37° C. in the presence of 5% $CO_2$ before being recultured.

Example 2

Enzymes, Bacteria, Plasmids and Molecular Biology Techniques

The restriction enzymes, the Taq polymerase for the chain amplification reactions, and the other enzymes required for the various DNA modifications were supplied, respectively, by New England Biolabs Inc., Roche Diagnostics and Gibco-BRL.

All these enzymes were used according to the manufacturers' recommendations. The standard molecular biology techniques were performed as described in "Molecular Biology: A Laboratory Manual", 2nd edition, (Sambrook et al., Cold Spring Harbor Laboratory, New York, 1989).

The BJ5183 competent bacteria (Hanahan D., J. Mol. Biol. 1983, 166, 557–580) were prepared as follows: 60 ml of a culture of these bacteria in the exponential phase were prepared according to the calcium chloride technique (Sambrook et al., 1989). They were harvested in a final volume of 2 ml of 50 mM $CaCl_2$. 300 µl of this bacterial suspension were mixed with the various homologous-recombination partner DNAs contained in a volume of 100 µl of 100 mM Tris-HCl pH 7.4 and left in contact for 30 min on melting ice, and the bacteria were then treated with a heat shock at +45° C. for 2 minutes, left to stand on melting ice for 10 minutes and finally plated out on a selective medium.

Example 3

Extraction of PAV-3 and PAV-5 Viral DNA

The viruses are cultured and amplified in 10 $cm^2$ Falcon flasks under the conditions of example 1. When the CPE is complete, the cells are harvested, lysed by 3 cycles of freezing/thawing and the viral suspension is then clarified by low-speed centrifugation. The PAV-3 and PAV-5 viruses are purified on a cesium chloride gradient (1.34 g/ml) and the viral band is harvested and purified and the viral DNAs are then obtained after treatment with proteinase K and extraction with phenol/chloroform (Sambrook et al., 1989). These DNAs are then used for the various cloning or polymerase chain amplification (PCA) steps.

Example 4

Construction of the "pITRs PAV3" Plasmid

The genomic DNA of the PAV-3 virus, prepared according to example 3, was digested with EcoRI and the 245-bp EcoRI D fragment was isolated after agarose gel electrophoresis. This fragment was then ligated with the pBlueScript KS plasmid (pBS-KS) (Stratagene Inc. La Jolla, Calif.) (GenBank # X52327), predigested with EcoRI and dephosphorylated, to give the plasmid referred to as "pKS-EcoDPAV3".

A PCA reaction was carried out with the pKS-EcoDPAV3 plasmid matrix and with the following oligonucleotides:

ITRPAV3 (SEQ ID NO: 1) (50-mer):

5'CCTTAATTAAGGTAGGGATAACAGGG-TAATCATCATCAATAATATACCGC 3' and

T3 (SEQ ID NO: 2) (20-mer):

5' ATTAACCCTCACTAAAGGGA 3'

The amplification product (367 bp) was treated with T4 DNA polymerase to make the ends blunt and was then digested with the ClaI enzyme and ligated with the pBS-KS plasmid, predigested with ClaI and EcoRV, to give the plasmid referred to as "pKS-Right ITR3" (FIG. 1).

The EcoRI D fragment was then freed from the pKS-Right ITR3 plasmid by digestion with the enzymes BamHI and KpnI, and the 353-bp BamHI-KpnI restriction fragment was ligated with the pPolyII plasmid (Lathe R. et al., Gene, 1987, 57, 193–201) (GenBank # G209113), predigested with BamHI and KpnI, to generate the plasmid referred to as "pPolyII-Right ITR3" (FIG. 1). The genomic DNA of the PAV-3 virus, prepared according to example 3, was digested with KpnI in order to isolate, after agarose gel electrophoresis, the 939-bp KpnI F terminal fragment. This fragment was ligated with the pBS-KS plasmid, predigested with KpnI and dephosphorylated, to give the plasmid referred to as "pKS-KpnFPAV3".

A PCA reaction was then carried out with the pKS-KpnFPAV3 plasmid matrix and with the following oligonucleotides:

ITRPAV3 (SEQ ID NO: 1) (50-mer):

5 CCTTAATTAAGGTAGGGATAACAGGGTAATCATCATCAATAATATACCGC 3' and

T7 (SEQ ID NO: 3):

5' TAATACGACTCACTATAGGG 3'

The amplification product (1086 bp) was treated with T4 DNA polymerase to make the ends blunt and was then digested with the XhoI enzyme and ligated with the pPolyII-Right ITR3 plasmid, predigested with BglII, treated with T4 DNA polymerase and then digested with XhoI, to generate the plasmid referred to as "pITRsPAV3" (FIG. 1).

Example 5

Construction of the pPAV3 Plasmid

The pITRsPAV3 plasmid (example 4) was linearized by digestion with ClaI and then co-transformed in BJ5183 competent bacteria with the PAV-3 virus genomic DNA prepared according to example 2. This co-transformation made it possible to generate, by homologous recombination in *Escherichia coli* (Chartier C. et al., J. Virol. 1996, 70, 4805–4810), a plasmid containing the complete cloned genome of PAV-3. This plasmid was designated as "pPAV3".

Example 6

Construction of the PAV-3 Shuttle Plasmids 6.1. Construction of the Plasmid with a Deletion of 622 Base Pairs (Small Deletion) in the E3 Region The pNEB193 plasmid (New England BioLabs Cat # 305-1) was digested with PacI, treated with T4 DNA polymerase and then self-religated to generate the "pNEBPac-" plasmid.

The pPAV3 plasmid (example 5) was digested with KpnI and BamHI to isolate the 4344-bp KpnI-BamHI fragment containing the E3 region (Reddy et al., Virology, 1998, 251, 414–426). This fragment was ligated with the pNEBPac-plasmid, predigested with KpnI and BamHI, to give the "pE3PAV3" plasmid (FIG. 2). The sequence of the KpnI-BamHI fragment was checked and was found to be identical to the sequence published by Reddy P. et al. (Virus Research, 1995, 36, 97–106 and Virology, 1998, 251, 414–426) (GenBank AN # U10433 and AN # AF083132) Those skilled in the art may refer to these references.

The pEGFP-F plasmid (Chalfie M. et al., Science, 1994, 263, 802–805; Clontech Cat # 6074-1) was modified in order to completely remove the polylinker. This deletion was obtained by digestion with BamHI, followed by a treatment with T4 DNA polymerase. Self-religation of the vector thus modified generated the pCMV-EGFP plasmid. The pCMV-EGFP plasmid was then digested with the AsnI and MluI enzymes and then treated with T4 DNA polymerase, to isolate the 1.6-kbp AsnI (blunt end)-MluI (blunt end) fragment (=CMV-EGFP expression cassette). This fragment was ligated with the pE3PAV3 plasmid, predigested with BsrGI and SnaBI and treated with T4 DNA polymerase, to generate the pE3dl622CMV-EGFP plasmid (FIG. 2). The deletion created between the BsrGI and SnaBI sites of the E3 region of the PAV-3 virus is 622 base pairs in size. This deletion extends from nucleotides 1002 to 1624 of the sequence published by P. Reddy et al. (Virus Research, 1995, 36, 97–106) (GenBank AN # U10433).

The pCMV-gD plasmid (Ambriovic A. et al., Virology, 1997, 238, 327–335) was digested with SnaBI and ClaI to isolate the 1.8-kbp SnaBI-ClaI fragment (containing the 3' portion of the CMV promoter and the PRV gD gene). This fragment was then treated with T4 DNa polymerase to make the ends blunt and was then ligated with the pE3dl622CMV-EGFP plasmid, predigested with SnaBI and HpaI, to generate the pE3dl622CMV-gD plasmid (FIG. 2).

6.2. Construction of the Plasmid with a Deletion of 919 Base Pairs (Large Deletion) in the E3 Region The pE3PAV3 plasmid (see section 6.1. above) was digested with SgrAI and SacI to isolate the 644-bp SgrAI-SacI fragment. This fragment was treated with T4 DNA polymerase to make the ends blunt and was then ligated with the pNEBPac-plasmid (6.1. above), predigested with EcoRI, treated with T4 DNA polymerase and then digested with SacI, to generate the pSgrAI-SacI plasmid.

The pE3PAV3 plasmid was digested with SnaBI and HindIII to isolate the 2.4-kbp SnaBI-HindIII fragment. This fragment was ligated with the pSgrAI-SacI plasmid, predigested with PmeI and HindIII, to generate the pE3dl919 plasmid (FIG. 3). The deletion created between the SacI and SnaBI sites of the E3 region of the PAV-3 virus is 919 base pairs in size. This deletion extends from nucleotides 706 to 1624 of the sequence published by P. Reddy et al. (Virus Research, 1995, 36, 97–106) (GenBank AN # U10433).

The pCMV-gD plasmid (example 6.1) was digested with SnaBI and ClaI to isolate the 1.8-kbp SnaBI-ClaI fragment. This fragment was then treated with the Klenow fragment of DNA polymerase to make the ends blunt and was then ligated with the pCMV-EGFP plasmid (example 6.1), predigested with SnaBI and HpaI and then dephosphorylated, to generate the pgD plasmid (FIG. 4).

The pCMV-EGFP plasmid (example 6.1) was digested with AsnI and MluI to isolate the 1.8-kbp AsnI-MluI fragment (CMV-EGFP cassette). This fragment was treated with the Klenow fragment of DNA polymerase to make the ends blunt and was then ligated with the pE3dl919 plasmid, predigested with AscI, treated with the Klenow fragment of DNA polymerase to make the ends blunt and then dephosphorylated, to generate the pE3dl919CMV-EGFP plasmid (FIG. 5).

The pgD plasmid (above) was digested with AsnI and MluI to isolate the 2.3-kbp AsnI-MluI fragment. This fragment was treated with T4 DNA polymerase to make the ends blunt and was then ligated with the pE3dl919 plasmid, predigested with AscI and treated with the Klenow fragment of DNA polymerase to make the ends blunt and then dephosphorylated, to generate the pE3dl919CMV-gD plasmid (FIG. 5).

Example 7

Construction of the Recombinant Genomes pPAV3dl622CMV-EGFP and pPAV3dl622CMV-gD

The pE3dl622CMV-EGFP plasmid (example 6.1) was digested with KpnI and BamHI to isolate the 5.5-kbp KpnI-BamHI fragment. This fragment was co-transformed in BJ5183 competent bacteria with the pPAV3 plasmid (example 5) linearized by digestion with the SnaBI enzyme.

This co-transformation led to the generation, by homologous recombination in *Escherichia coli*, of the pPAV3dl622CMV-EGFP plasmid.

The pE3CMVgD plasmid (example 6.1) was digested with EcoRI and PmeI to isolate the 6.0-kbp EcoRI-PmeI fragment. This fragment was co-transformed in BJ5183 competent bacteria with the pPAV3 plasmid (example 5) linearized by digestion with the SnaBI enzyme. This co-transformation led to the generation, by homologous recombination in *Escherichia coli*, of the pPAV3dl622CMVgD plasmid.

Example 8

Construction of the Recombinant Genomes pPAV3dl919CMV-EGFP and pPAV3dl919CMV-gD

The pE3dl919CMV-EGFP plasmid (example 6.2) was linearized with HindIII and then co-transformed in BJ5183 competent bacteria with the pPAV3 plasmid (example 5) linearized by digestion with the SnaBI enzyme. This co-transformation led to the generation, by homologous recombination in *Escherichia coli*, of the pPAV3dl919CMV-EGFP plasmid.

The pE3dl919CMV-gD plasmid (example 6.2) was linearized with HindIII and then co-transformed in BJ5183 competent bacteria with the pPAV3 plasmid (example 5) linearized by digestion with the SnaBI enzyme. This co-transformation led to the generation, by homologous recombination in *Escherichia coli*, of the pPAV3dl919CMV-gD plasmid.

Example 9

Construction of the Recombinant Genomes pPAV3dl622EGFP, pPAV3dl622gD, pPAV3dl919EGFP and pPAV3dl919gD (Insertion of the Coding Sequences without the CMV Promoter Sequences)

9.1. Construction of the pE3dl622EGFP and pE3dl919EGFP Plasmids

Figure 6:
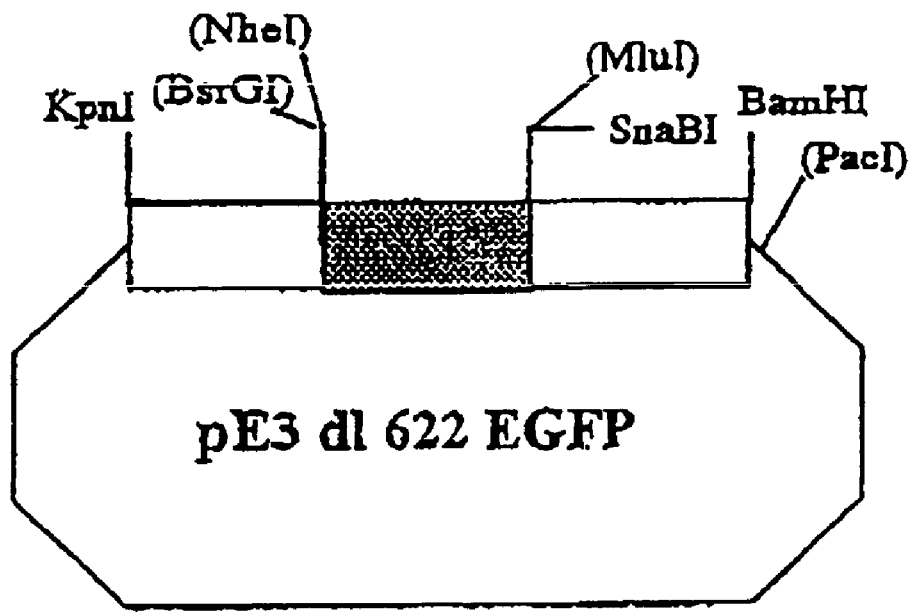
Figure 6:
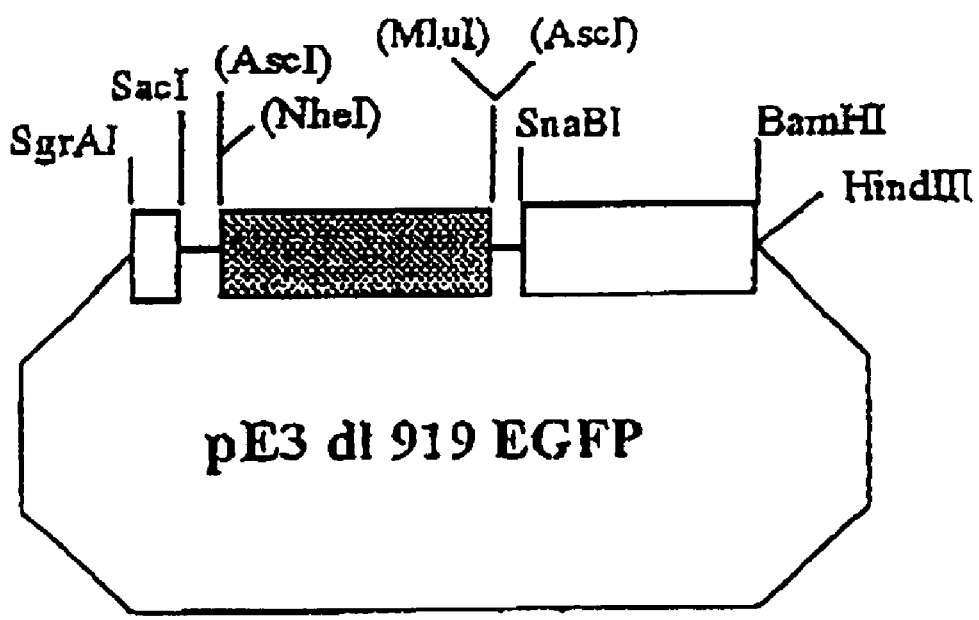

The pCMV-EGFP plasmid (example 6.1) was digested with NheI and MluI to isolate the 1.0-kbp NheI-MluI fragment. This fragment was treated with the Klenow fragment of DNA polymerase to make the ends blunt and then ligated with the pE3PAV3 plasmid (example 6.1), predigested with BsrGI, treated with the Klenow fragment of DNA polymerase and finally digested with SnaBI, to generate the pE3dl622EGFP plasmid (FIG. 6).

The pCMV-EGFP plasmid was digested with NheI and MluI to isolate the 1.0-kbp NheI-MluI fragment. This fragment was treated with the Klenow fragment of DNA polymerase to make the ends blunt and was then ligated with the pE3dl919 plasmid, predigested with AscI, treated with the Klenow fragment of DNA polymerase and then dephosphorylated, to generate the pE3dl919EGFP plasmid (FIG. 6).

9.2. Construction of the pE3dl622gD and pE3dl919gD Plasmids

Figure 7:
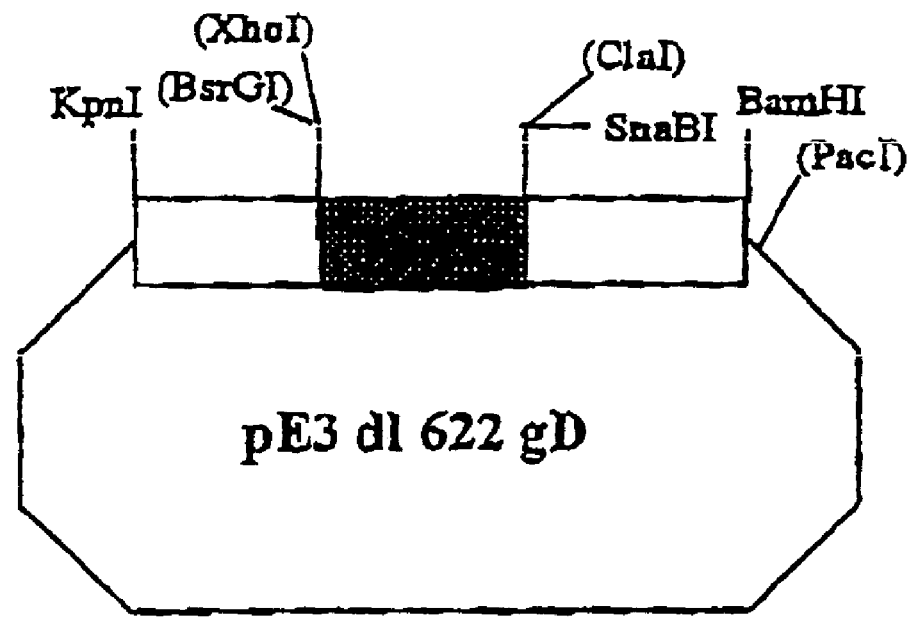
Figure 7:
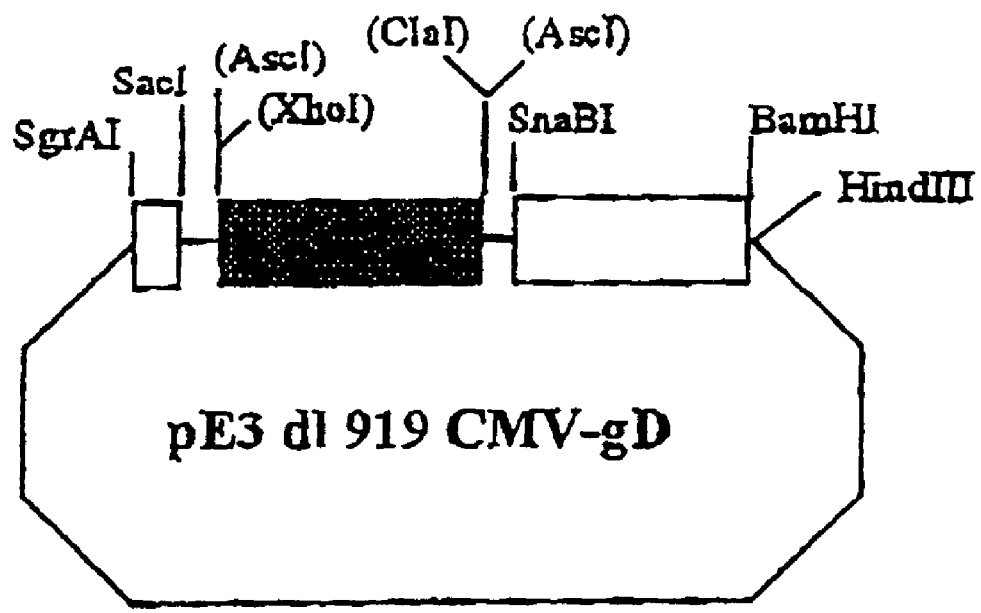

The pgD plasmid (example 6.2) was digested with XhoI and ClaI to isolate the 1.5-kbp XhoI-ClaI fragment. This fragment was treated with the Klenow fragment of DNA polymerase to make the ends blunt and was then ligated with the pE3PAV3 plasmid (example 6.1), predigested with BsrGI, treated with the Klenow fragment of DNA polymerase and then digested with SnaBI, to generate the pE3dl622gD plasmid (FIG. 7).

The pgD plasmid (example 6.2) was digested with XhoI and ClaI to isolate the 1.5-kbp XhoI-ClaI fragment. This fragment was treated with the Klenow fragment of DNA polymerase to make the ends blunt and was then ligated with the pE3dl919 plasmid (example 6.2), predigested with AscI, treated with the Klenow fragment of DNA polymerase and finally dephosphorylated, to generate the pE3dl919gD plasmid (FIG. 7).

9.3. Construction of the pPAV73dl622EGFP, pPAV3dl622gD, pPAV3dl919EGFP and pPAV3dl919gD Plasmids The pE3dl622EGFP plasmid (example 9.1) was digested with KpnI and BamHI and then co-transformed in BJ5183 competent bacteria with the pPAV3 plasmid (example 5), prelinearized by digestion with SnaBI. This co-transformation made it possible to generate, by homologous recombination in *Escherichia coli*, the pPAV3dl622EGFP plasmid.

The pE3dl622gD plasmid (example 9.2) was digested with EcoRI and PmeI and then co-transformed in BJ5183 competent bacteria with the pPAV3 plasmid (example 5), prelinearized by digestion with SnaBI. This co-transformation generated, by homologous recombination in *Escherichia coli*, the pPAV3dl622gD plasmid.

The pE3dl919EGFP plasmid (example 9.1) was linearized by digestion with HindIII and then co-transformed in BJ5183 competent bacteria with the pPAV3 plasmid (example 5), prelinearized by digestion with SnaBI. This co-transformation generated, by homologous recombination in *Escherichia coli*, the pPAV3dl919EGFP plasmid.

The pE3dl919gD plasmid (example 9.2) was linearized by digestion with HindIII and then co-transformed in BJ5183 competent bacteria with the pPAV3 plasmid (example 5), prelinearized by digestion with SnaBI. This co-transformation generated, by homologous recombination in *Escherichia coli*, the pPAV3dl919gD plasmid.

Example 10

Production of Recombinant PAV3 Viruses by Transfection with the Recombinant PAV3 Genomes Cloned into *Escherichia coli*

PK-15 or ST cells (see example 1) are transfected in 6-well plates to a confluence density of 60–80% with 2 µg of recombinant PAV-3 genomic DNA, predigested with PacI, diluted in the presence of 4 to 12 µl of LipofectAMINE (Gibco-BRL Cat # 18324-012) depending on the cell line.

After transfection according to the conditions recommended by the supplier, the cells are left in culture for a few days until the appearance of a viral CPE. A further cell culture passage is then carried out to amplify the recombinant virus obtained.

The transfection carried out with the pPAV3dl622CMV-EGFP plasmid (example 7) generated the recombinant virus vPAV3-1.

The transfection carried out with the pPAV3dl622CMV-gD plasmid (example 7) generated the recombinant virus vPAV3-2.

The transfection carried out with the pPAV3dl919CMV-EGFP plasmid (example 8) generated the recombinant virus vPAV3-3.

The transfection carried out with the pPAV3dl919CMV-gD plasmid (example 8) generated the recombinant virus vPAV3-4

The transfection carried out with the pPAV3dl622EGFP plasmid (example 9.3) generated the recombinant virus vPAV3-5.

The transfection carried out with the pPAV3dl622gD plasmid (example 9.3) generated the recombinant virus vPAV3-6.

The transfection carried out with the pPAV3dl919EGFP plasmid (example 9.3) generated the recombinant virus vPAV3-7.

The transfection carried out with the pPAV3dl919gD plasmid (example 9.3) generated the recombinant virus vPAV3-8.

Example 11

Construction of the pITRsPAV5 Plasmid 11.1. Cloning of the Right-Terminal Genomic Fragment The genomic DNA of the PAV-5 virus, prepared according to example 3, was digested with EcoRI and the 0.9-kbp EcoRI I right-terminal fragment was isolated after agarose gel electrophoresis. This fragment was ligated with the pBS-KS plasmid, predigested with EcoRI and dephosphorylated, to generate the "pKS-Right ITR5" plasmid.

A PCA reaction was then carried out with the pKS-Right ITR5 plasmid matrix and with the following oligonucleotides:

ITRPAV5 (SEQ ID NO: 4) (50-mer):

5'CCTTAATTAAGGTAGGGATAACAGGG-TAATCATCATCAATAATATACGGA 3' and T3 (SEQ ID NO: 2) (20-mer)

Figure 8:
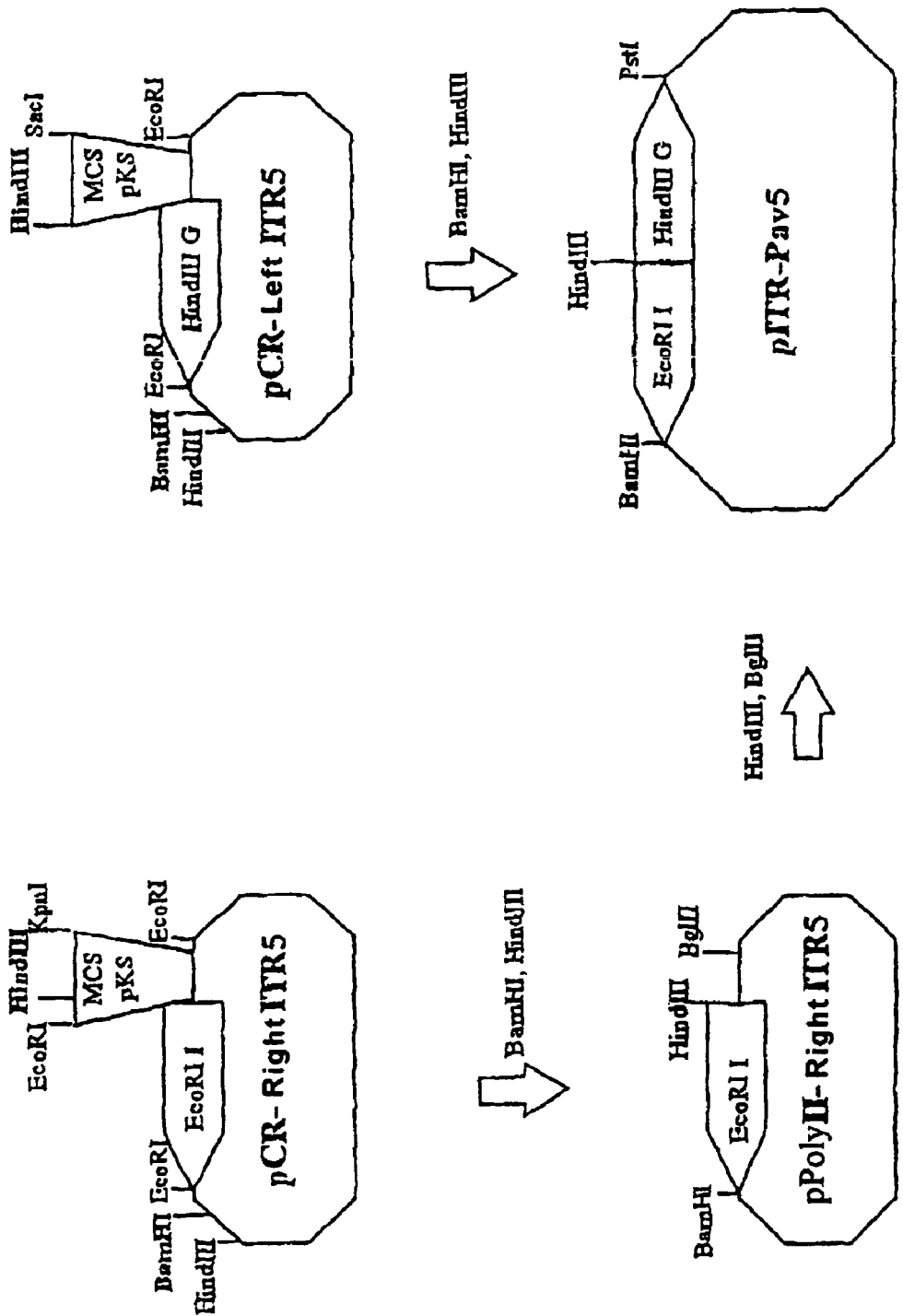

5' ATTAACCCTCACTAAAGGGA 3' to produce a 1.0-kbp fragment. This fragment was ligated with the pCRII plasmid (InVitrogen Original TA Cloning Kit Cat # K2000-01) to give the "pCR-Right ITR5" plasmid (FIG. 8).

11.2. Cloning of the Left-Terminal Genomic Fragment

The genomic DNA of the PAV-5 virus, prepared according to example 3, was digested with HindIII and the 1.2-kbp HindIII left-terminal fragment was isolated after agarose gel electrophoresis. This fragment was ligated with the pBS-KS plasmid, predigested with HindIII and dephosphorylated, to generate the "pKS-Left ITR5" plasmid.

A PCA reaction was then carried out with the pKS-Left ITR5 plasmid matrix and with the following oligonucleotides:

ITRPAV5 (SEQ ID NO: 4):

5'CCTTAATTAAGGTAGGGATAACAGGG-TAATCATCATCAATAATATACGGA 3' and T7 (SEQ ID NO: 3 20-mer):

5' TAATACGACTCACTATAGGG 3' to produce a 1.3-kbp fragment. This fragment was ligated with the pCRII plasmid to give the "pCR-Left ITR5" plasmid (FIG. 8).

11.3. Construction of the pPolyII-Right ITR5 Plasmid

The pCR-Right ITR5 plasmid (example 11.1) was digested with BamHI and HindIII to isolate the 1.0-kbp BamHI-HindIII fragment. This fragment was then ligated with the pPolyII plasmid (see example 4), predigested with BamHI and HindIII, to generate the "pPolyII-Right ITR5" plasmid (FIG. 8).

11.4. Construction of the pITRsPAV5 Plasmid

The pCR-Left ITR5 plasmid (example 11.2) was digested with BamHI and HindIII to isolate the 1.3-kbp BamHI-HindIII fragment. This fragment was then ligated with the pPolyII-Right ITR5 plasmid, predigested with BglII and HindIII, to generate the "pITRs PAV5" plasmid (FIG. 8).

Example 12

Construction of the pPAV5 Plasmid

The pITRsPAV5 plasmid was linearized by digestion with HindIII. The fragment obtained was then co-transformed in BJ5183 competent bacteria with the genomic DNA of the PAV-5 virus prepared according to example 3. This co-transformation generated, by homologous recombination, a plasmid containing all of the genome of the PAV-5 virus. This plasmid was denoted as "pPAV5".

Example 13

Figure 9:
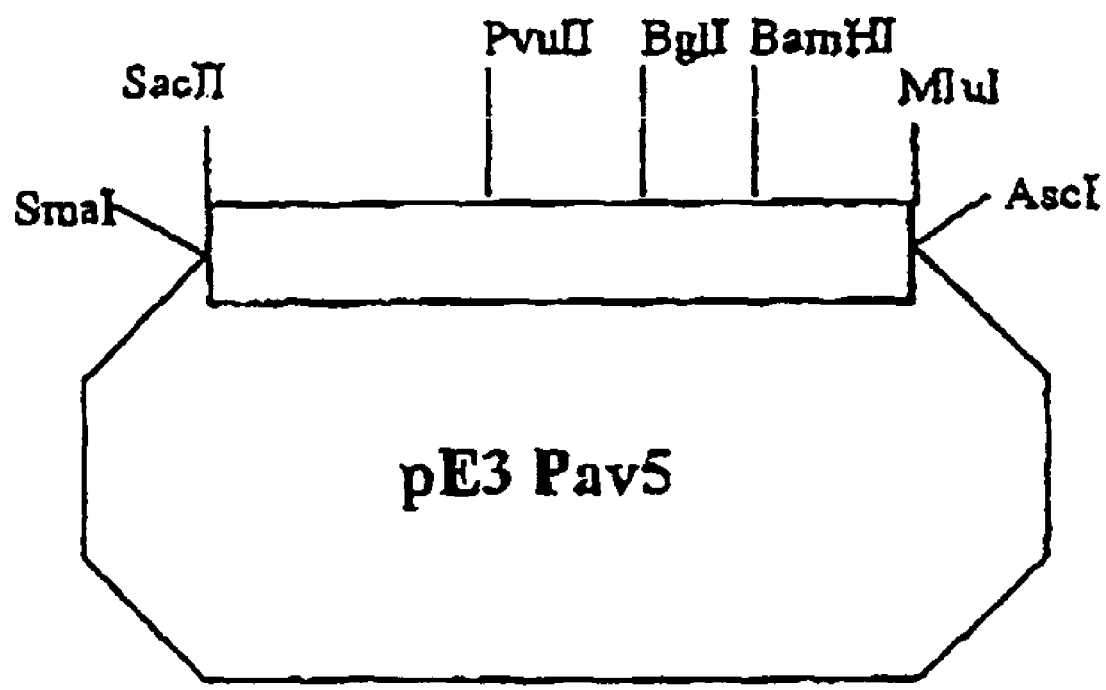

Construction of the PAV-5 Shuttle Plasmids 13.1. Construction of the E3 PAV-5 Shuttle Plasmid The pPAV5 plasmid (example 12) was digested with SacI and MluI to isolate the 4372-bp SacI-MluI fragment containing the E3 region. This fragment was ligated with the pNEB193 plasmid (example 6.1), predigested with SmaI and AscI, to give the "pE3PAV5" plasmid (FIG. 9).

The SacI-MluI fragment cloned into the pE3PAV5 plasmid was entirely sequenced and analyzed. The analysis of this sequence and of the adjacent sequences present on the pPAV5 plasmid confirmed that the cloned fragment did indeed represent the E3 region of the PAV-5 virus. The sequence of this region (5614 base pairs) (SEQ ID NO: 5) is given in FIG. 13.

13.2. Construction of the Donor CMV-EGFP and CMV-PRV gD Plasmids with a Deletion of 1472 Base Pairs in the E3 Region.

Figure 10:
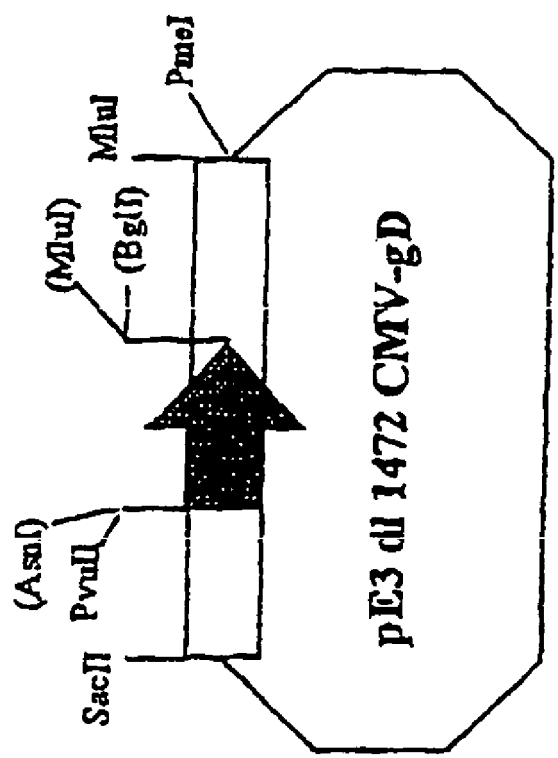
Figure 10:
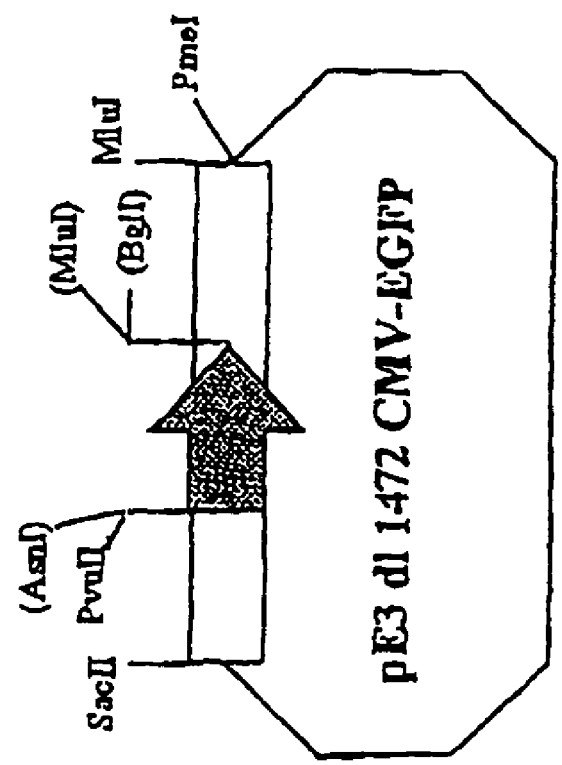

The pCMV-EGFP plasmid (example 6.1) was digested with the AsnI and MluI enzymes and then treated with T4 DNA polymerase to isolate the 1.6-kbp AsnI (blunt end)-MluI (blunt end) fragment. This fragment was ligated with the pE3PAV5 plasmid (example 13.1), predigested with PvuII and BglI, and treated with T4 DNA polymerase, to generate the pE3dl1472CMV-EGFP plasmid (FIG. 10). The deletion introduced between the PvuII and BglI sites is 1472 bp in size. This deletion is between nucleotides 2389 and 3861 of the sequence given in FIG. 13 (SEQ ID NO: 5).

The pgD plasmid (example 6.1) was digested with the AsnI and MluI enzymes to isolate the 2.3-kbp AsnI-MluI fragment. This fragment was then treated with T4 DNA polymerase to make the ends blunt and was then ligated with the pE3PAV5 plasmid, predigested with PvuII and BglI, and treated with T4 DNA polymerase, to generate the pE3dl1472CMVgD plasmid (FIG. 10).

Figure 11:
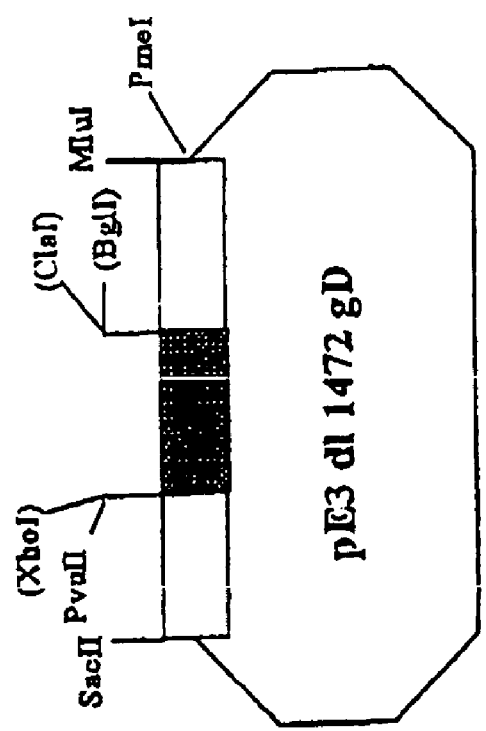
Figure 11:
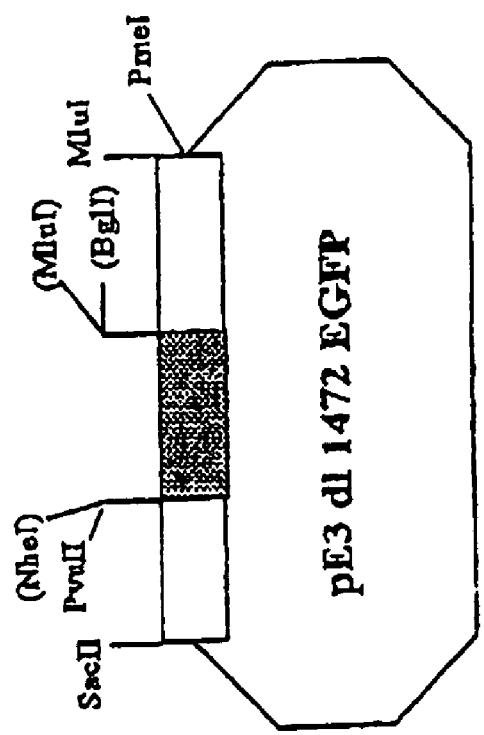

The pCMV-EGFP plasmid was digested with NheI and MluI to isolate the 1.0-kbp NheI-MluI fragment. This fragment was treated with the Klenow fragment of DNA polymerase to make the ends blunt and was then ligated with the pE3PAV5 plasmid, predigested with PvuII and BglI, and treated with T4 DNA polymerase, to generate the pE3dl1472EGFP plasmid (FIG. 11).

The pCMVgD plasmid (example 6.1) was digested with XhoI and ClaI to isolate the 1.5-kbp XhoI-ClaI fragment. This fragment was treated with the Klenow fragment of DNA polymerase to make the ends blunt and was then ligated with the pE3PAV5 plasmid, predigested with PvuII and BglI, and treated with T4 DNA polymerase, to generate the pE3dl1472gD plasmid (FIG. 12).

Example 14

Figure 12:

Construction of the Recombinant Genomes pPAV5dl1472CMV-EGFP and pPAV5dl1472CMV-gD The pE3dl1472CMV-EGFP plasmid (example 13.2) was linearized with PmeI and then co-transformed in BJ5183 competent bacteria with the pPAV5 plasmid (example 12) linearized by partial digestion with the BamHI enzyme (site of joining of the restriction subfragments BamHI A-BamHI D, FIG. 12). This co-transformation generated, by homologous recombination in *Escherichia coli*, the pPAV5dl1472CMV-EGFP plasmid.

The pE3dl1472CMVgD plasmid (example 13.2) was linearized with PmeI and then co-transformed in BJ5183 competent bacteria with the pPAV5 plasmid (example 12) linearized by partial digestion with the BamHI enzyme (site of joining of the restriction subfragments BamHI A-BamHI D, FIG. 12). This co-transformation generated, by homologous recombination in *Escherichia coli*, the pPAV5dl1472CMV-gD plasmid.

Example 15

Construction of the Recombinant Genomes pPAV5dl1472EGFP and pPAV5dl1472 gD (Insertion of the Coding Sequences without the CMV Promoter Sequences)

The pE3dl1472EGFP plasmid (example 13.2) was linearized with PmeI and then co-transformed in BJ5183 competent bacteria with the pPAV5 plasmid (example 12) linearized by partial digestion with the BamHI enzyme (site of joining of the restriction subfragments BamHI A-BamHI D, FIG. 12). This co-transformation generated, by homologous recombination in *Escherichia coli*, the pPAV5dl1472EGFP plasmid.

The pE3dl1472gD plasmid (example 13.2) was linearized with PmeI and then co-transformed in BJ5183 competent bacteria with the pPAV5 plasmid (example 12) linearized by partial digestion with the BamHI enzyme (site of joining of the restriction subfragments BamHI A-BamHI D, FIG. 12). This co-transformation generated, by homologous recombination in *Escherichia coli*, the pPAV5dl1472gD plasmid.

Example 16

Production of Recombinant PAV-5 Viruses by Transfection with the Recombinant PAV-5 Genomes Cloned into *Escherichia coli*

PK-15 or ST cells (see example 1) are transfected in 6-well plates to a confluence density of 60–80% with 2 µg of recombinant PAV-5 genomic DNA, predigested with PacI, diluted in the presence of 4 to 12 µl of LipofectAMINE (Gibco-BRL Cat # 18324-012) depending on the cell lines.

After transfection according to the conditions recommended by the supplier, the cells are left in culture for a few days until the appearance of a viral CPE. A passage is then carried out to amplify the recombinant virus obtained.

The transfection carried out with the pPAV5dl1472CMV-EGFP plasmid (example 14) generated the recombinant virus vPAV5-1.

The transfection carried out with the pPAV5dl1472CMV-gD plasmid (example 14) generated the recombinant virus vPAV5-2.

The transfection carried out with the pPAV5dl1472EGFP plasmid (example 15) generated the recombinant virus vPAV5-3.

The transfection carried out with the pPAV5dl1472gD plasmid (example 15) generated the recombinant virus vPAV5-4.

Example 19

Manufacture of the Vaccines According to the Invention

The recombinant viruses obtained according to the invention are cultured and amplified in PK-15 cell cultures. The supernatants are harvested after a complete cytopathogenic effect has been observed. After clarification by low-speed centrifugation to remove the cell debris, followed by centrifugation to concentrate the virions and washing of the viral pellet, the pellet is taken up in a solution of culture medium. The viral titer of these suspensions is measured. The viral titer is then optionally adjusted by dilution so as to obtain a final viral titer of between $10^4$ 50% cell culture infective doses ($CCID_{50}$) and $10^7$ $CCID_{50}$/ml.

The viral suspensions can then be frozen, or preferably lyophilized in the presence of a lyophilization substrate.

Example 20

Vaccination of Pigs

After thawing or after taking up the lyophilized doses in water for injectable preparations, and optional addition of an adjuvant, pigs are vaccinated with doses of from $10^4$ to $10^7$ $CCID_{50}$ of each recombinant virus. The vaccines comprise one or more recombinant PAV viruses each expressing different immunogens.

The vaccines are administered either by injection with a needle (intramuscular route) in a volume of 2 ml, or mucosally (intranasally or by ocular instillation) (volumes adapted to each route).

The intradermal injections can also be carried out using a needle-free injector such as the PIGJET device (Société Endoscoptic, Laon, France).

Example 21

Protocol for Vaccination/Testing for Pseudorabies

A vaccination/testing protocol was used to evaluate the efficacy of a vaccine consisting of a suspension of the adjuvant-free recombinant vPAV3-2 virus (example 10 of the present invention).

Groups of six 8–10 week-old piglets, born from sows which had been vaccinated against pseudorabies virus (PRV) at the start of gestation, were established. All the piglets definitely had maternal anti-PRV antibodies on day D0 of the vaccination. The piglets of groups 1 and 2 were vaccinated on D0 intranasally with 1 milliliter (ml) of a suspension of the recombinant virus vPAV3-2 (PAV-3/PRV gD) having a titer of $10^7$ $CCID_{50}$/ml (0.5 ml per nostril). Group 2 was vaccinated in the same way, but also received a second administration on D21. Group 3 received on D0, intramuscularly, 1 ml of a viral suspension of PAV-3/gD with a titer of $10^7$ $CCID_{50}$/ml. Group 4 was vaccinated in the same way as Group 3, but received a second injection of viral suspension on D21. Group 5 was not vaccinated and served as a negative control group for the test.

All the groups were tested on D35 by administration of 2 ml (1 ml per nostril) of a suspension of the PRV NIA3 strain at a titer of at least $10^{7.3}$ pfu/ml.

After testing, the pigs were monitored on the basis of the criteria of weight change (delta G7) (Stellmann C. et al., J. Biol. Standard, 1989, 17, 1–11) (D0 to D7 after testing) and of the level of viral excretion via the nasal mucosae, and on the basis of ELISA antibody titers and anti-PRV seroneutralizing titers.

It should be clearly understood that the invention defined by the attached claims is not limited to the specific embodiments indicated in the description above, but encompasses the variants which depart neither from the context nor from the spirit of the present invention.

The invention claimed is:

1. A recombinant in vivo replication competent porcine adenovirus (PAV) serotype 5 (PAV-5) which contains at least one heterologous nucleic acid molecule encoding at least one product in the E3 region of the PAV-5 genome, whereby the recombinant PAV replicates in vivo and expresses the product.

2. The recombinant PAV according to claim 1, wherein the PAV has a deletion in the E3 region.

3. A recombinant in vivo replication competent porcine adenovirus (PAV) serotype 5 (PAV-5) which contains at least one heterologous nucleic acid molecule encoding at least one product in the E3 region of the PAV-5 genome, wherein the heterologous nucleic acid molecule is within nucleotides 2064 to 4083 in SEQ ID NO: 5 and whereby the recombinant PAV replicates in vivo and expresses the product.

4. The recombinant PAV of claim 3, wherein the heterologous nucleic acid molecule is within nucleotides 2389 to 3861 in SEQ ID NO: 5.

5. The recombinant PAV of claim 3, wherein the heterologous nucleic acid molecule is within nucleotides 2382 to 4042 in SEQ ID NO: 5.

6. A recombinant in vivo replication competent porcine adenovirus (PAV) serotype 5 (PAV-5) which contains at least one heterologous nucleic acid molecule encoding at least one product in the E3 region of the PAV-5 genome, wherein the heterologous nucleic acid molecule is in place of nucleotides 2389–3861 in SEQ ID NO: 5 and whereby the recombinant PAV replicates in vivo and expresses the product.

7. The recombinant PAV of claim 6, wherein the heterologous nucleic acid molecule is in place of nucleotides 2064–4083 in SEQ ID NO: 5.

8. The recombinant PAV of claim 6, wherein the heterologous nucleic acid molecule is in place of nucleotides 2382–4042 in SEQ ID NO: 5.

9. The recombinant PAV according to any of claims 1, 3 or 6, wherein the heterologous nucleic acid molecule encodes an immunogen or an immunologically active fragment thereof or an epitope thereof, of a porcine pathogen; or an immunomodulator; or an immunogen or an immunologically active fragment thereof or an epitope thereof, of a porcine pathogen, and an immunomodulator.

10. The recombinant PAV according to any of claims 1, 3 or 6, containing more than one heterologous nucleic acid molecule.

11. The recombinant PAV according to any of claims 1, 3 or 6, wherein the heterologous nucleic acid molecule encodes a polyepitope.

12. The recombinant PAV according to any of claims 1, 3 or 6, containing an IRES sequence.

13. The recombinant PAV according to any of claims 1, 3 or 6, wherein the heterologous nucleic acid molecule encodes a product from a porcine pathogenic agent selected from the group consisting of viruses, bacteria and parasites.

14. The recombinant PAV according to claim 13, wherein the porcine pathogenic agent is selected from the group consisting of pseudorabies virus, swine influenza virus, porcine reproductive and respiratory syndrome virus, parvovirus virus, Hog Cholera Virus, porcine circovirus type 2, *Actinobacillus pleuropneumoniae* and *Mycoplasma hyopneumoniae*.

15. The recombinant PAV according to claim 13, wherein the porcine pathogenic agent is pseudorabies virus.

16. The recombinant PAV according to claim 13, wherein the porcine pathogenic agent is swine influenza virus.

17. The recombinant PAV according to claim 13, wherein the porcine pathogenic agent is porcine reproductive and respiratory syndrome virus.

18. The recombinant PAV according to claim 13, wherein the porcine pathogenic agent is parvovirus.

19. The recombinant PAV according to claim 13, wherein the porcine pathogenic agent is Hog Cholera Virus.

20. The recombinant PAV according to claim 13, wherein the porcine pathogenic agent is porcine circovirus type 2.

21. The recombinant PAV according to claim 13, wherein the porcine pathogenic agent is *Actinobacillus pleuropneumoniae*.

22. The recombinant PAV according to claim 13, wherein the porcine pathogenic agent is *Mycoplasma hyopneumoniae*.

23. The recombinant PAV according to claim 13, wherein the heterologous nucleic acid molecule(s) encode(s): pseudorabies virus gB, pseudorabies virus gC, pseudorabies virus gD, swine influenza HA, swine influenza NA, swine influenza NP, ORF4 of porcine reproductive and respiratory syndrome virus, ORF7 gene porcine reproductive and respiratory syndrome virus, Hog Cholera Virus E1, Hog Cholera Virus E2 gene, parvovirus VP2, porcine circovirus type 2 ORF1, or porcine circovirus type 2 ORF2.

24. The recombinant PAV according to claim 13, wherein the heterologous nucleic acid molecule(s) encode(s) an immunologically active fragment(s) or epitope(s) of: pseudorabies virus gB, pseudorabies virus gC, pseudeorabies virus gD, swine influenza HA, swine influenza NA, swine influenza NP, ORF4 of porcine reproductive and respiratory syndrome virus, ORF7 gene porcine reproductive and respiratory syndrome virus, Hog Cholera Virus E1, Hog Cholera Virus E2 gene, parvovirus VP2, porcine circovirus type 2 ORF1, or porcine circovirus type 2 ORF2.

25. The recombinant PAV according to claim 13, wherein the heterologous nucleic acid molecule(s) encode(s) porcine circovirus type 2 (PCV2) ORF1 or PCV2 ORF2 or PCV2 ORF 1 and PCV ORF2.

26. The recombinant PAV according to claim 13, wherein the heterologous nucleic acid molecule(s) encode(s) pseudorabies virus gB or pseudorabies virus gC or pseudorabies virus gD or pseudorabies virus gB and gC or pseudorabies virus gB, gC and gD.

27. The recombinant PAV according to claim 13, wherein the heterologous nucleic acid molecule(s) encode swine influenza HA or swine influenza NA or swine influenza NP or swine influenza HA and NA and NP.

28. The recombinant PAV according to claim 13, wherein the heterologous nucleic acid molecule encodes porcine parvovirus VP2.

29. The recombinant PAV according to claim 13, wherein the heterologous nucleic acid molecule encodes porcine respiratory and reproductive virus ORF6.

30. The recombinant PAV according to claim 13, wherein the heterologous nucleic acid molecule encodes Hog Cholera Virus E1 or Hog Cholera Virus E1 and E2.

31. The recombinant PAV according to any of claims 1, 3 or 6, wherein the heterologous nucleic acid molecule encodes a porcine cytokine.

32. The recombinant PAV according to claim 31, wherein the porcine cytokine is selected from the group consisting of GM-CSF, IL-4, IL-12 and IL-18.

33. A porcine vaccine comprising at least one recombinant PAV according to claim any of claims 1, 3 or 6, and a veterinarily acceptable vehicle or excipient.

34. The porcine vaccine of claim 33, comprising more than one recombinant PAV, wherein the recombinant PAVs comprise different heterologous nucleic acid molecules and a veterinarily acceptable vehicle or excipient.

35. The porcine vaccine according to claim 33, which contains an adjuvant.

36. The porcine vaccine according to claim 35, wherein the adjuvant is an acrylic or methacrylic acid polymer, or a copolymer of maleic anhydride and an alkenyl derivative.

37. The porcine vaccine of claim 36, wherein the adjuvant is a carbomer.

38. The porcine vaccine of claim 36, wherein the adjuvant is EMA.

39. An in vivo replication competent porcine adenovirus (PAV) serotype 5 (PAV-5) comprising a nucleotide sequence as depicted in SEQ ID NO: 5, which contains at least one deletion in the E3 region of the PAV-5 genome, whereby the recombinant PAV replicates in vivo.

40. The recombinant PAV of claim 39, wherein the deletion is in a region comprising nucleotides 2389 to 3861 in SEQ ID NO: 5.

41. The recombinant PAV of claim 39, wherein the deletion is of nucleotides 2389 and 3861 in SEQ ID NO: 5.

42. The recombinant PAV of claim 39, wherein the deletion is in a region comprising nucleotides 2064 to 4083 in SEQ ID NO: 5.

43. The recombinant PAV of claim 39, wherein the deletion is of nucleotides 2064 and 4083 in SEQ ID NO: 5.

44. The recombinant PAV of claim 39, wherein the deletion is in a region comprising nucleotides 2382 to 4042 in SEQ ID NO: 5.

45. The recombinant PAV of claim 39, wherein the deletion is of nucleotides 2382 and 4042 in SEQ ID NO: 5.

* * * * *